(12) United States Patent
Shiba

(10) Patent No.: US 9,339,413 B2
(45) Date of Patent: May 17, 2016

(54) DRAINAGE DEVICE

(76) Inventor: Hiroharu Shiba, Osaka (JP)

( * ) Notice: Subject to any disclaimer, the term of this patent is extended or adjusted under 35 U.S.C. 154(b) by 0 days.

(21) Appl. No.: 14/001,415

(22) PCT Filed: Feb. 24, 2012

(86) PCT No.: PCT/JP2012/054589
§ 371 (c)(1),
(2), (4) Date: Oct. 30, 2013

(87) PCT Pub. No.: WO2012/115233
PCT Pub. Date: Aug. 30, 2012

(65) Prior Publication Data
US 2014/0052110 A1    Feb. 20, 2014

(30) Foreign Application Priority Data
Feb. 26, 2011    (JP) .................................. 2011-041007

(51) Int. Cl.
*A61M 27/00*    (2006.01)
*A61F 9/007*    (2006.01)
(Continued)

(52) U.S. Cl.
CPC ............. *A61F 9/007* (2013.01); *A61B 17/0231* (2013.01); *A61F 9/00772* (2013.01); *A61M 1/008* (2013.01); *A61M 25/02* (2013.01); *A61M 2025/0213* (2013.01); *A61M 2027/004* (2013.01)

(58) Field of Classification Search
CPC ..................... A61M 25/02; A61M 2025/0213; A61M 2025/024; A61M 2210/0612; A61M 1/008; A61M 25/00; A61M 2025/00; A61M 2027/00; A61M 2027/004; A61F 9/00

USPC .......................................... 606/205; 604/541
See application file for complete search history.

(56) References Cited

U.S. PATENT DOCUMENTS 2,117,312 A * 5/1938 Gauly ............................... 606/1
4,579,116 A * 4/1986 Catalano ....................... 606/107
(Continued)

FOREIGN PATENT DOCUMENTS

JP    08-164162 A    6/1996
JP    08-317939 A    12/1996
(Continued)

OTHER PUBLICATIONS

Japanese Office Action issued by the Japanese Patent Office in connection with Japanese Application No. JP 2011-041007, on May 6, 2013.

*Primary Examiner* — Leslie Deak
*Assistant Examiner* — Kai Weng
(74) *Attorney, Agent, or Firm* — Fitzpatrick, Cella, Harper & Scinto

(57) ABSTRACT

A drainage device for discharging a liquid retained in a palpebral fissure to the outside of the palpebral fissure includes a hook portion that is bent into a hook to be hooked on a lid margin or a medical drape and comes into contact with the liquid in the palpebral fissure or overflowing from the palpebral fissure to form a start point of a flow path for the liquid, and a body portion that extends from the hook portion and discharges the liquid guided by the hook portion. The distal end of the hook portion is formed into a spatula shape. The body portion includes an abdominal portion and a tail portion and discharges the liquid after arrival thereof at a surface of the tail portion by making the liquid run along a gap between a lid margin side surface of the abdominal portion and the lid margin or the medical drape.

10 Claims, 32 Drawing Sheets

(51) Int. Cl.
*A61M 25/02* (2006.01)
*A61M 1/00* (2006.01)
*A61B 17/02* (2006.01)

(56) References Cited

U.S. PATENT DOCUMENTS

| | | | | |
|---|---|---|---|---|
| 4,863,457 | A | * | 9/1989 | Lee ........................... 604/891.1 |
| 5,586,531 | A | | 12/1996 | Vittorio ......................... 123/320 |
| 5,618,278 | A | | 4/1997 | Rothrum ........................ 604/356 |
| 5,928,662 | A | * | 7/1999 | Phillips ........................ 424/427 |
| 6,544,169 | B2 | * | 4/2003 | Putrino et al. ................ 600/236 |
| 7,175,594 | B2 | * | 2/2007 | Foulkes ........................ 600/236 |
| 2006/0124139 | A1 | * | 6/2006 | Morris ........................... 128/849 |
| 2010/0268013 | A1 | * | 10/2010 | Larsen et al. ..................... 600/3 |

FOREIGN PATENT DOCUMENTS

| | | | | |
|---|---|---|---|---|
| JP | H 9-184433 A | | 7/1997 | |
| JP | H 10-9854 A | | 1/1998 | |
| JP | 2000-060895 A | | 2/2000 | |
| JP | 2005-237895 A | | 9/2005 | |
| JP | 2198816 | * | 6/2010 | ............. A61F 9/007 |
| WO | 2009/031319 A1 | | 3/2009 | |

* cited by examiner

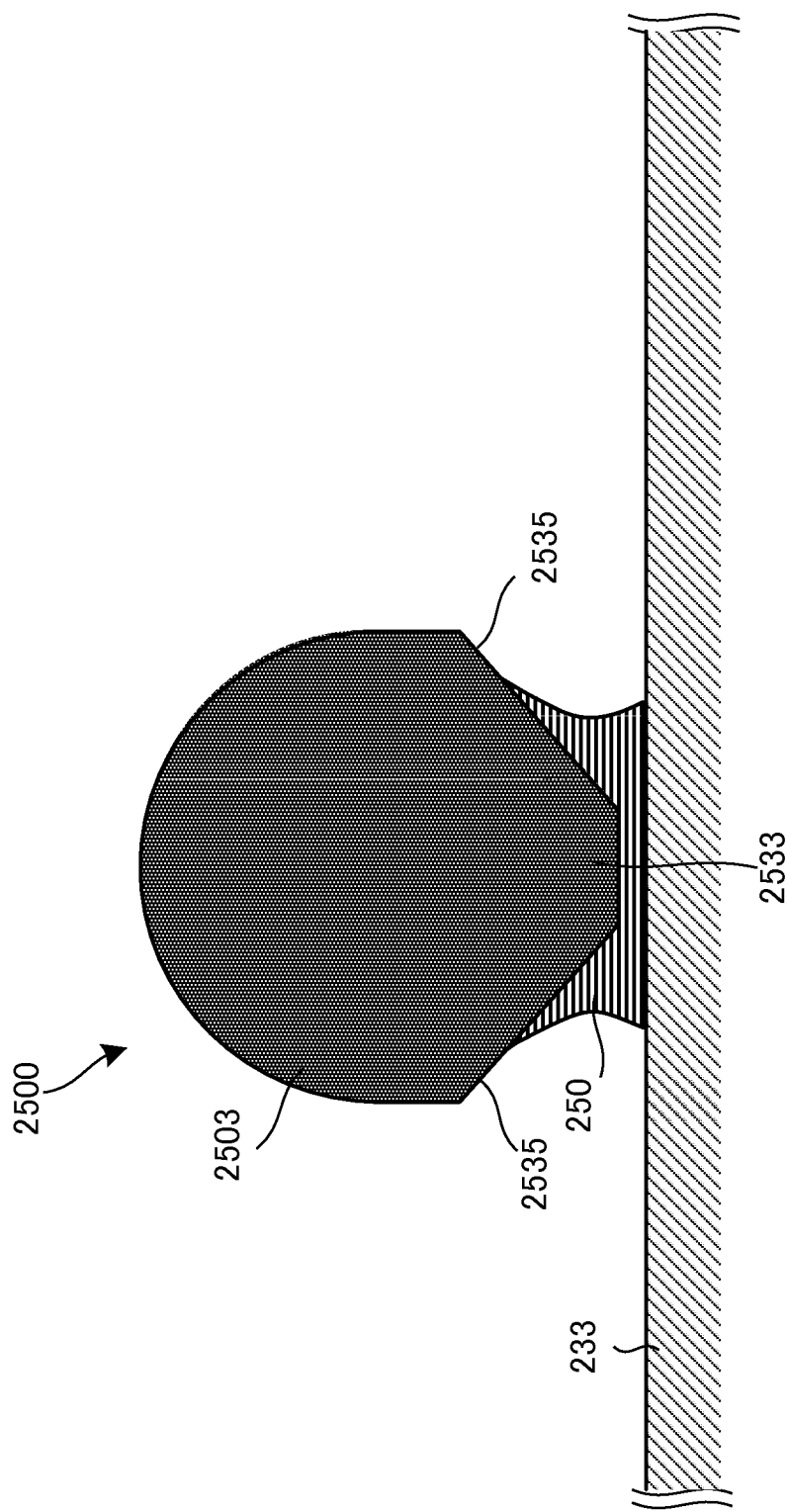

DRAINAGE DEVICE

CROSS REFERENCE TO RELATED APPLICATION

The present application is a national-stage entry under 35 U.S.C. 371 of International Application No. PCT/JP2012/054589 filed on Feb. 24, 2012, and claims the benefit of foreign priority under 35 U.S.C. 119 of Japanese Application No. 2011-041007, filed on Feb. 26, 2011.

TECHNICAL FIELD

The present invention relates to a technique for discharging a liquid retained in a palpebral fissure to the outside of the palpebral fissure.

BACKGROUND ART

In the above technical field, as disclosed in patent literature 1, there is known a technique of discharging the liquid stored in the palpebral fissure to the outside by an aspirator.

CITATION LIST

Patent Literature

Patent literature 1: Japanese Patent Laid-Open No. 2000-60895

SUMMARY OF THE INVENTION

Technical Problem

However, the above conventional technique needs to use an electric aspirator, and hence lacks in convenience. In addition, this technique requires an assistant who handles the aspirator, and the skill of the assistant influences the suction efficiency. This may pose a problem to the operation itself.

The present invention enables to provide a technique of solving the above problem.

Solution to Problem

One aspect of the present invention provides a drainage device for discharging a liquid retained in a palpebral fissure to the outside of the palpebral fissure, comprising a hook portion that is bent into a hook to be hooked on a lid margin or a medical drape and comes into contact with the liquid in the palpebral fissure or overflowing from the palpebral fissure to form a start point of a flow path for the liquid, and a body portion that extends from the hook portion and discharges the liquid guided by the hook portion, wherein a distal end of the hook portion is formed into a spatula shape, and the body portion includes an abdominal portion and a tail portion and discharges the liquid after arrival thereof at a surface of the tail portion by making the liquid run along a gap between a lid margin side surface of the abdominal portion and the lid margin or medical drape.

The width of the hook portion having the spatula shape is smaller than the width of the thickest portion of the body portion.

The body portion includes an inclined surface inclined, relative to an axis, from a connecting portion with the hook portion toward a rear surface.

The body portion has a nearly circular cross-section taken along a plane perpendicular to the axis.

The body portion has a nearly polygonal cross-section taken along a plane perpendicular to the axis.

The body portion includes a grip portion on a rear side thereon.

Advantageous Effects of Invention

According to the present invention, it is possible to easily discharge the liquid retained in the palpebral fissure to the outside of the palpebral fissure without using any aspirator.

BRIEF DESCRIPTION OF THE DRAWINGS

FIG. 25C is a sectional view showing a state of use of the drainage device according to the 12th embodiment of the present invention;

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Structure of Drainage Device

Figure 1:
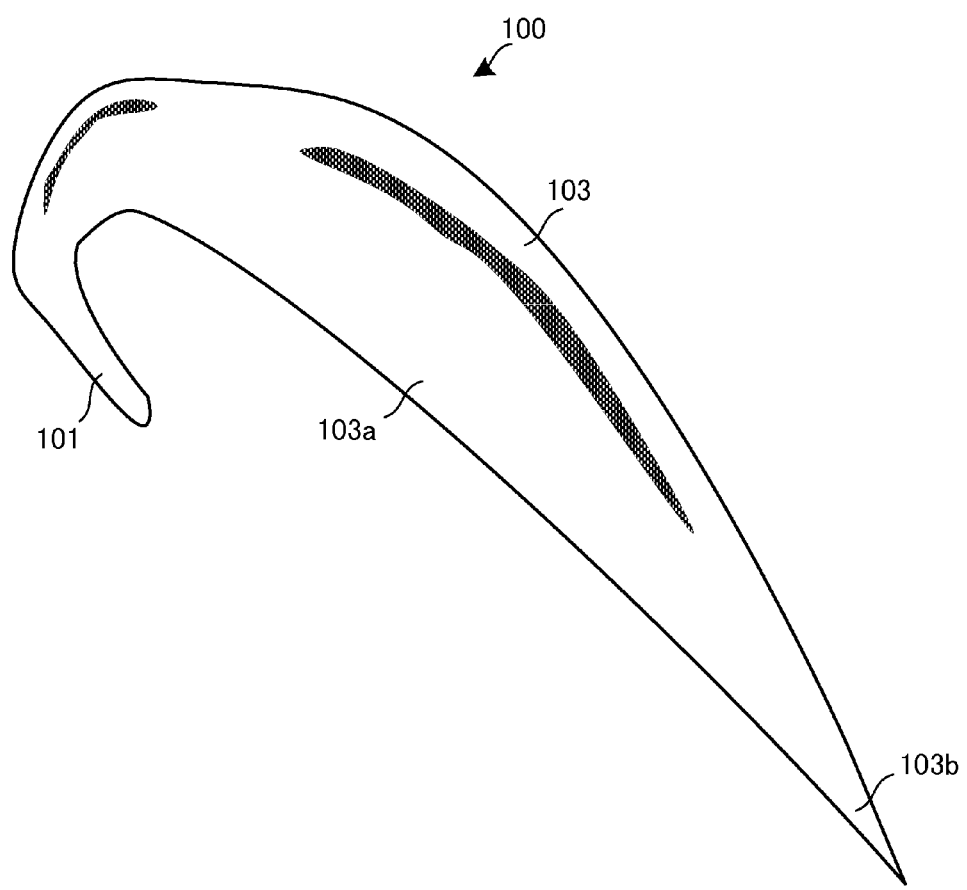
FIG. 1 is a view showing the arrangement of a drainage device according to the first embodiment of the present invention.

The structure of a drainage device 100 according to the first embodiment of the present invention will be described with reference to FIG. 1. FIG. 1 is a view showing the arrangement of the drainage device 100 according to this embodiment. The drainage device 100 is a device used to discharge a liquid retained in a palpebral fissure to the outside of the palpebral fissure.

As shown in FIG. 1, the drainage device 100 includes a hook portion 101 and a body portion 103. The hook portion 101 is bent into a hook to be hooked on the lid margin or medical drape, and comes into contact with the liquid in the palpebral fissure or the liquid overflowing from the palpebral fissure to form the start point of the liquid flow path. The body portion 103 extends from the hook portion 101, has a spindle shape, and discharges the liquid guided by the hook portion 101. The body portion 103 includes an abdominal portion 103a and a tail portion 103b.

With the above arrangement, the drainage device 100 according to this embodiment discharges the liquid which comes into contact with the hooked hook portion 101 from the tail portion 103b by making the liquid run along the abdominal portion 103a of the body portion 103. It is therefore possible to simply and easily discharge a liquid without using any aspirator.

State of Use of Drainage Device

Figure 2A:
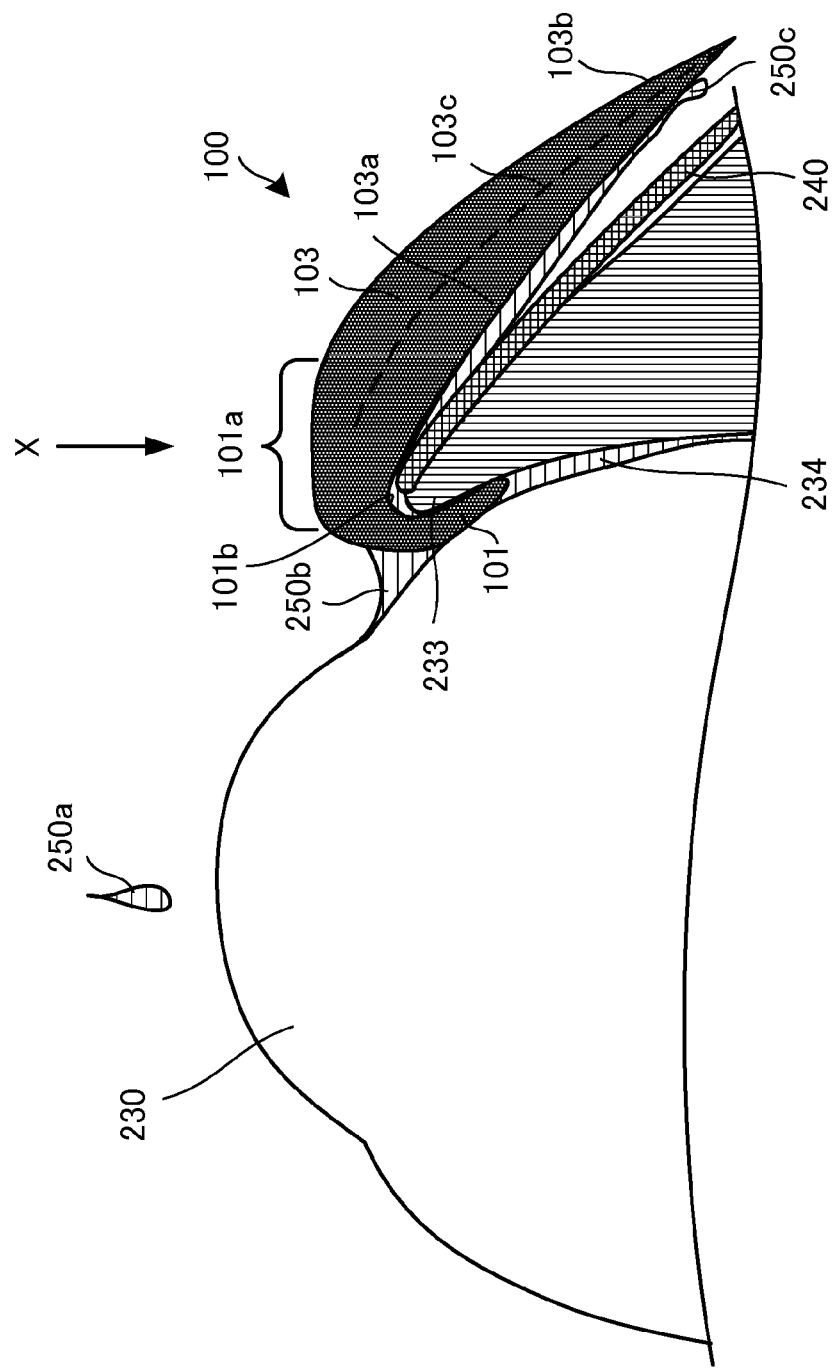
FIG. 2A is a sectional view showing a state of use of the drainage device according to the first embodiment of the present invention.
Figure 2B:
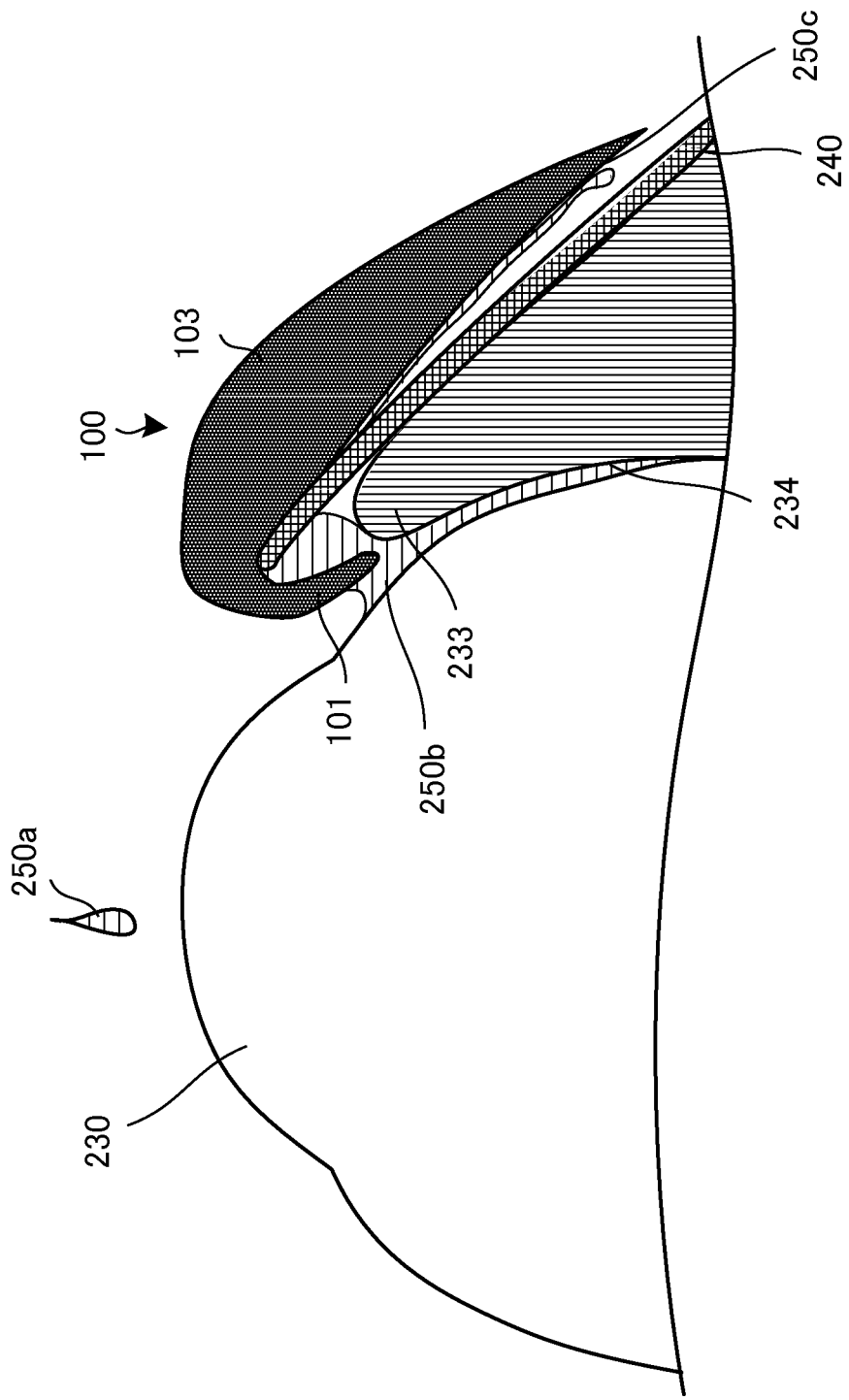
FIG. 2B is a sectional view showing another state of use of the drainage device according to the first embodiment of the present invention.
Figure 3:
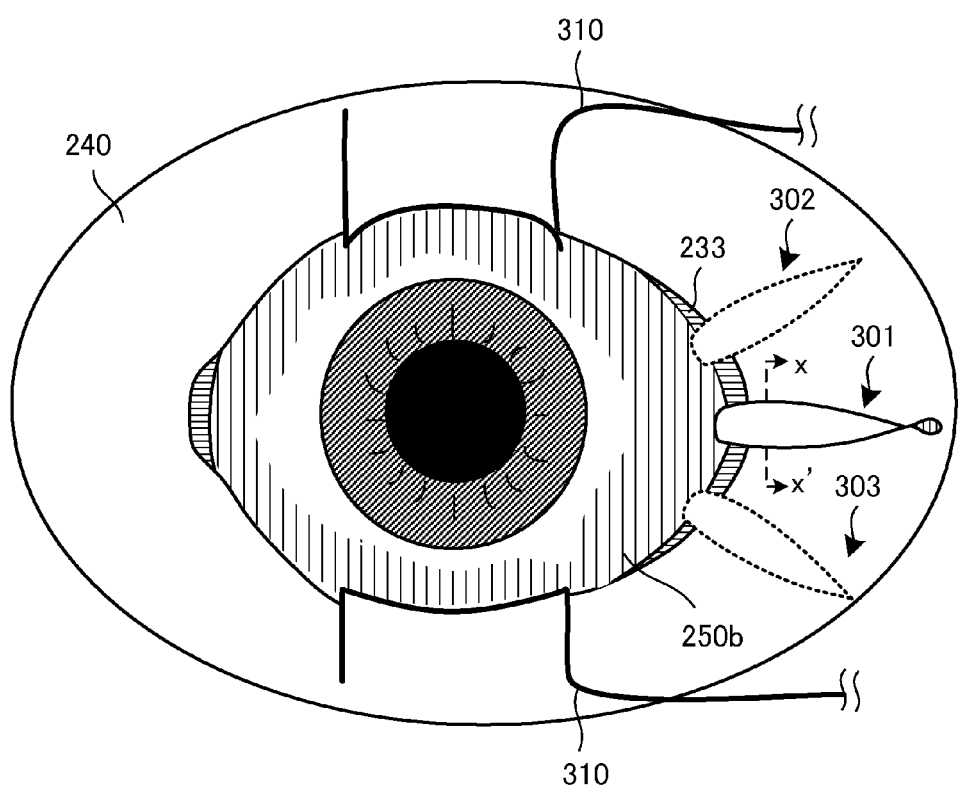
FIG. 3 is a plan view showing a state of use of the drainage device according to the first embodiment of the present invention.
Figure 4:
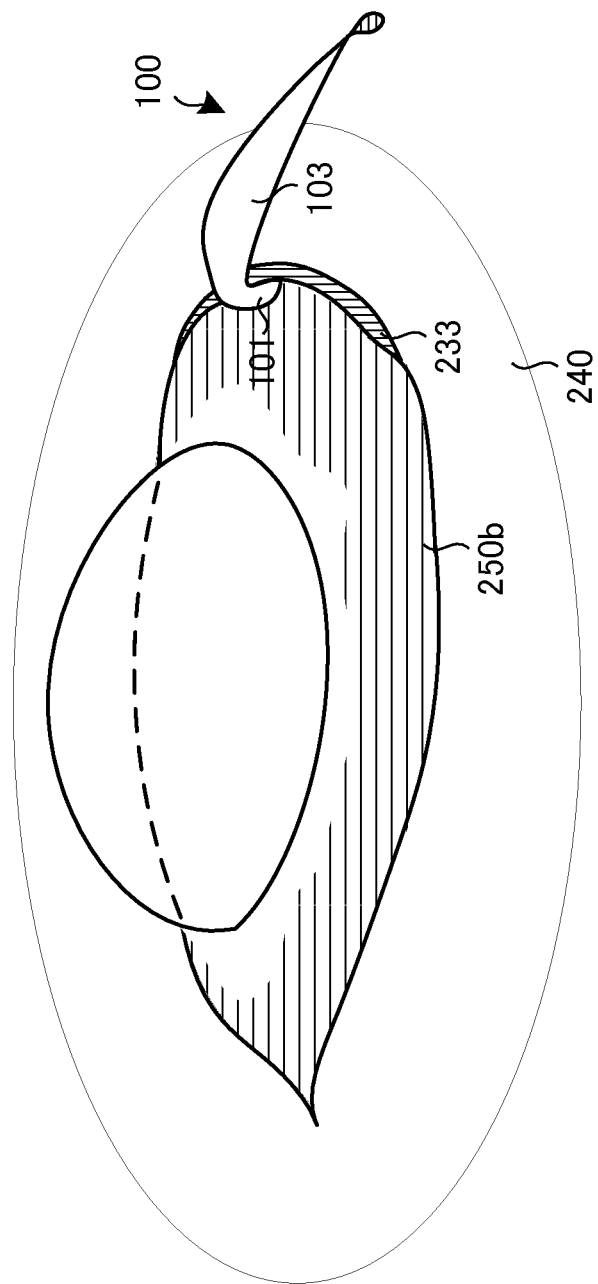
FIG. 4 is a perspective view showing a state of use of the drainage device according to the first embodiment of the present invention.
Figure 5:
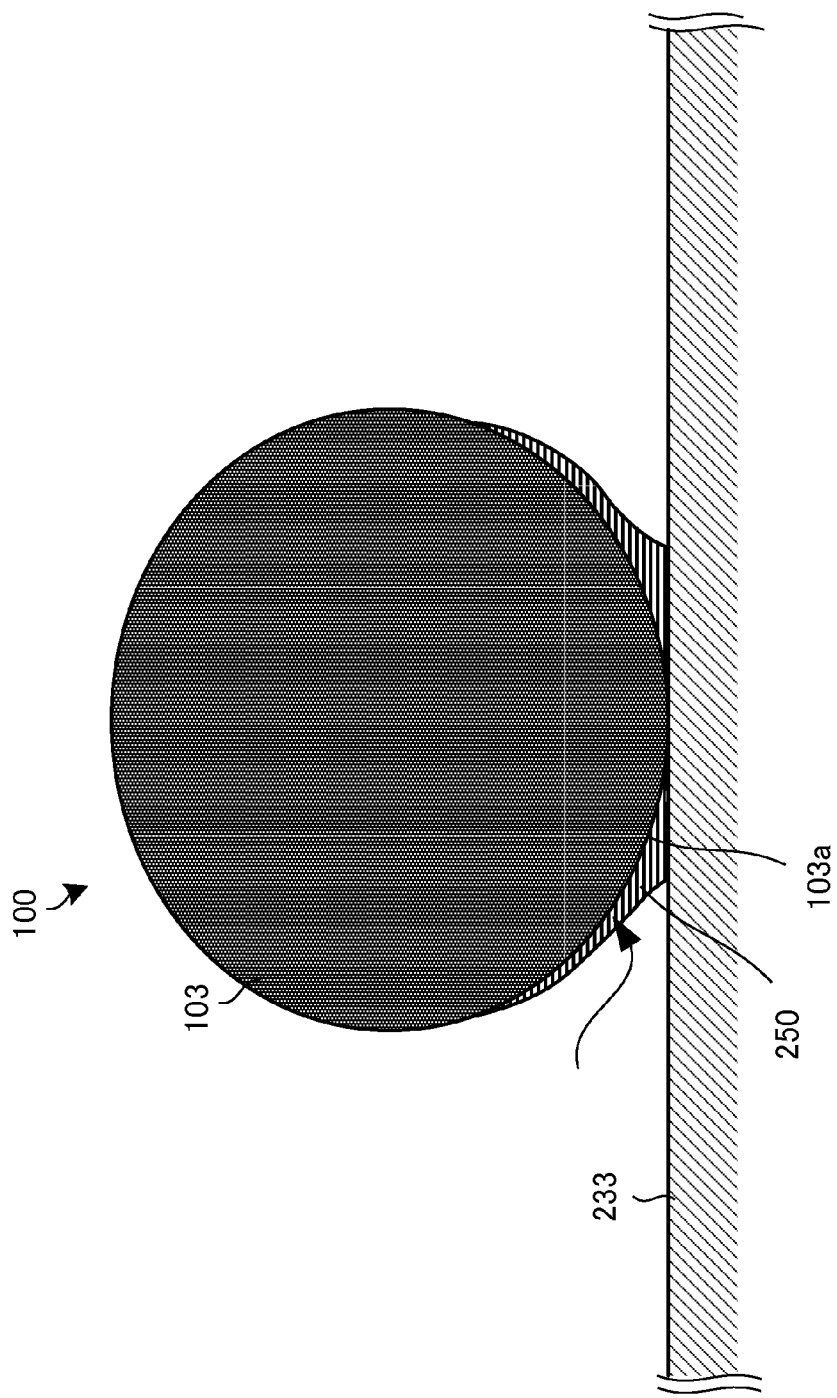
FIG. 5 is a sectional view showing a state of use of the drainage device according to the first embodiment of the present invention.

A state of use of the drainage device 100 will be described with reference to FIGS. 2A, 23, 3, 4, and 5. FIG. 2A shows an example of a state of use of the drainage device 100 according to this embodiment. FIG. 2A is a sectional view of the palpebral fissure on which the drainage device is placed and a peripheral portion of the palpebral fissure, taken along a plane passing through the medial ocular angle and the lateral ocular angle. FIG. 2B shows another example of a state of use of the drainage device 100 according to the embodiment. FIG. 3 is a plan view showing a state of use of the drainage device 100. FIG. 4 is a perspective view showing a state of use of the drainage device 100. FIG. 5 is a sectional view of the drainage device 100, taken along a plane perpendicular to an axis 103c and viewed from the lid margin side.

As shown in FIG. 2A, the drainage device 100 is placed to be hooked on a conjunctival sac 234 on the lateral ocular angle side between an eyeball 230 and a lid margin 233. The drainage device 100 includes the hook portion 101 and the body portion 103. A medical drape 240 is a sheet-like cloth which encloses the lid margin 233 and an eyelash (not shown) to perform sterilization, and is provided with a hole corresponding to the eyeball portion. With reference to FIG. 2A, the drainage device 100 is placed such that the hook portion 101 and the body portion 103 sandwich the lid margin 233 and the medical drape 240.

As shown in FIG. 2A, the hook portion 101 of the drainage device 100 is inserted into the conjunctival sac 234. Note that a liquid 250a is eye-drops, saline, artificial aqueous humor, or the like, and liquids 250b and 250c are liquids with tears mixed with eye-drops, saline, artificial aqueous humor, and the like.

The distal end portion of the hook portion 101 is tapered to have a shape suitable to be inserted into the conjunctival sac 234. The distal end portion of the hook portion 101 may be formed to extend toward or away from the body portion 103.

When coming into contact with the hook portion 101 inserted into the conjunctival sac 234, the liquid 250b retained in the palpebral fissure is guided by the body portion 103 along the inner surface of the hook portion 101 and is discharged to the outside of the palpebral fissure along the tail portion of the body portion 103. The distal end portion of the hook portion 101 is preferably formed to be thinner than the thickest portion of the body portion 103.

A neck portion 101a located at the boundary between the hook portion 101 and the body portion 103 is cut to form a horizontal plane, when the drainage device 100 is used, to prevent a surgical tool or the like from contacting the drainage device 100 when being placed on the lid margin 233. That is, as shown in FIG. 2A, the neck portion 101a is cut into an almost flat shape when viewed from a direction X perpendicular to a section taken along a plane passing through the medial ocular angle and the lateral ocular angle. The inner side of the bent portion of the hook portion 101 is formed to have an a radius corner 101b.

With the above shape, the drainage device 100 discharges the liquid 250b running along the surface of the hook portion 101 from the tail portion 103b by making the liquid run along the bottom surface of the body portion 103.

FIG. 2B shows another example of a state of use of the drainage device 100 according to this embodiment. FIG. 2B is a sectional view of the palpebral fissure on which the drainage device 100 is placed and a peripheral portion of the palpebral fissure, taken along a plane passing through the medial ocular angle and the lateral ocular angle.

Referring to FIG. 2B, the drainage device 100 is placed such that the hook portion 101 is hooked on the medical drape 240. If it is difficult to insert and place the hook portion 101 of the drainage device 100 into the lid margin 233 of the patient, the drainage device 100 is used upon being hooked on the medical drape 240 as shown in FIG. 23. The hook portion 101 is hooked on the medical drape 240 placed at a position where it does not directly contact the lid margin 233. When the surface of the liquid 250b retained in the palpebral fissure comes into contact with the distal end portion of the hook portion 101, the hook portion 101 guides the liquid 250b to the body portion 103 so as to suck up the liquid by the capillary action between the hook portion 101 and the medical drape 240, thereby discharging the liquid from the tail portion 103b.

FIG. 3 is a view for explaining the installation position of the drainage device 100 when performing surgery with the upper and lower eyelids being vertically open by a lid retractor 310. In this state, the practitioner performs surgery while constantly dropping a liquid such as a saline on the eyeball. When performing intraocular surgery, the practitioner sometimes injects an artificial aqueous humor having high viscosity to maintain the intraocular pressure. Such a liquid is also retained at the cornea or conjunctival periphery in the palpebral fissure.

The liquid 250b retained in this manner sometimes disturbs the clearness of an operative field and makes it difficult to perform surgery. If the eye to be operated is a so-called recessed eye with a small eyelid width, in particular, such liquid retention causes a problem to surgery. It is possible to ensure the clearness of the operative field by placing the drainage device 100 on the lateral ocular angle side and discharging the liquid in the palpebral fissure.

The installation position of the drainage device 100 is not limited to a position 301 on a line passing through the medial ocular angle and the lateral ocular angle, and may be a position near the lateral ocular angle of the lid margin 233 at which the drainage device 100 can be hooked thereon. The drainage device 100 may be placed at a position 302 moved from a line passing through the medial ocular angle and the lateral ocular angle toward the forehead side along the lid margin 233. In addition, the drainage device 100 may be placed at a position 303 moved toward the cheek side along the lid margin 233. The installation position of the drainage device 100 is not limited to these positions and may be any position at which it is possible to discharge a liquid 250 to the outside of the palpebral fissure.

FIG. 4 is a perspective view showing a state of use of the drainage device 100. As shown in FIG. 4, the practitioner inserts and places the distal end portion of the hook portion 101 of the drainage device 100 in the conjunctival sac of the lid margin 233.

It is possible to smoothly discharge the liquid 250 from the lid margin 233 by keeping the tail portion 103b of the drainage device 100 at a position lower to the ear side than the position of the body portion 103 placed on the lid margin 233.

FIG. 5 is a sectional view of the drainage device 100, taken along a plane perpendicular to the axis 103c and viewed from a direction parallel to the axis 103c of the drainage device 100 on the palpebral fissure side.

As shown in FIG. 5, the body portion 103 of the drainage device 100 is in contact with the lid margin 233 to make the liquid 250 run along the abdominal portion 103a of the body portion 103. The surface of the abdominal portion 103a is round and has an almost circular section so as to have a shape suitable for the liquid 250 to run along the surface. If the flow rate of the liquid 250 increases, the contact point between the liquid 250 and the surface of the abdominal portion 103a of the body portion 103 moves in the upper direction in FIG. 5.

Mechanism of Drainage

As shown in FIG. 2A, when the liquid 250b in the palpebral fissure comes into contact with the hook portion 101, the liquid is discharged to the outside of the palpebral fissure along the surfaces of the hook portion 101 and body portion 103 owing to the adhesive force (surface tension) of the liquid 250b to the hook portion 101, the wettability of the surface of the hook portion 101, and capillary action. In this case, the surface tension is the force with which different kinds of substances attract each other when they come into contact with each other. In this embodiment, therefore, this force acts as the force with which the liquid 250 and the hook portion 101 as a solid substance attract each other when they come into contact with each other. Capillary action is a phenomenon in which the liquid inside a narrow tube ascends/descends in the tube. In the embodiment, the gap formed by the surface of the abdominal portion 103a of the body portion 103 and the medical drape 240 functions as a capillary tube, which guides the liquid 250b to the outside of the palpebral fissure.

If the drainage device 100 is hooked on the medical drape 240 as shown in FIG. 2B, as the amount of liquid 250b retained in the palpebral fissure gradually increases, the liquid level in the palpebral fissure gradually rises due to surface tension. As a consequence, the liquid comes into contact with the hook portion 101 inserted in the lid margin 233. In this case, the gap formed in the space defined by the body portion 103 and the medical drape 240 functions as a capillary tube, and the liquid 250c descends in the gap with the body portion 103 due to capillary action.

Shape of Drainage Device

Figure 6:
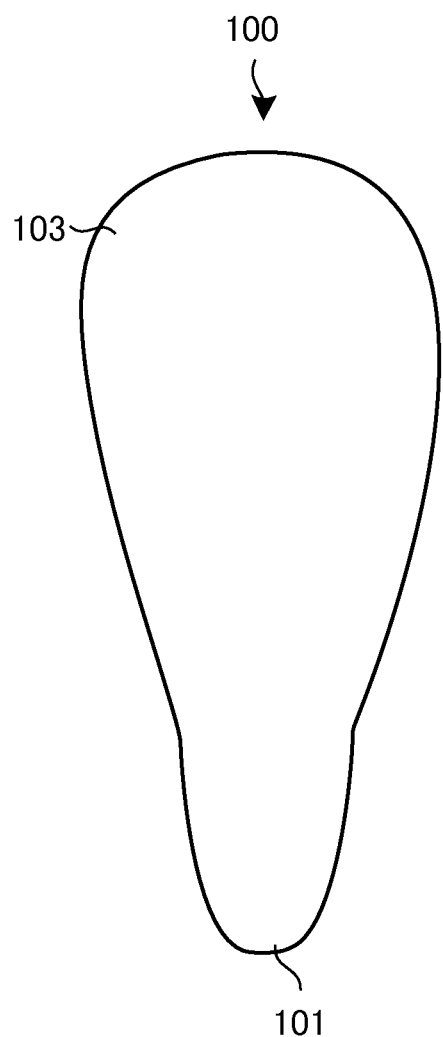
FIG. 6 is a front view of the drainage device according to the first embodiment of the present invention.

FIG. 6 is a front view of the drainage device 100. The drainage device 100 has a round shape as a whole when viewed from the front. Since the distal end portion of the hook portion 101 is bent at an acute angle toward the abdominal portion 103a of the body portion 103, the tip of the distal end portion cannot be seen from the front.

Figure 7:
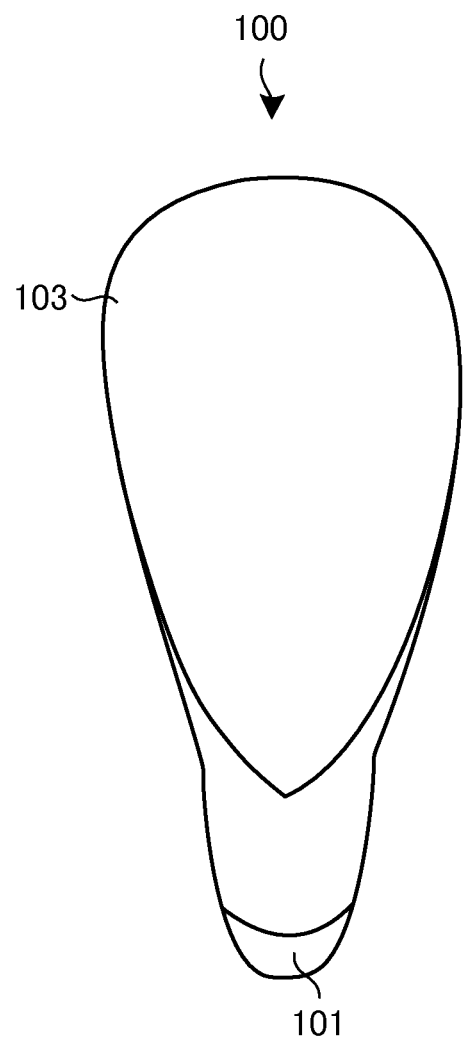
FIG. 7 is a rear view of the drainage device according to the first embodiment of the present invention.

FIG. 7 is a rear view of the drainage device 100. The distal end portion of the hook portion 101 is bent toward the abdominal portion of the body portion 103. The inner surface of the bent portion is formed into a curved surface.

Figure 8:
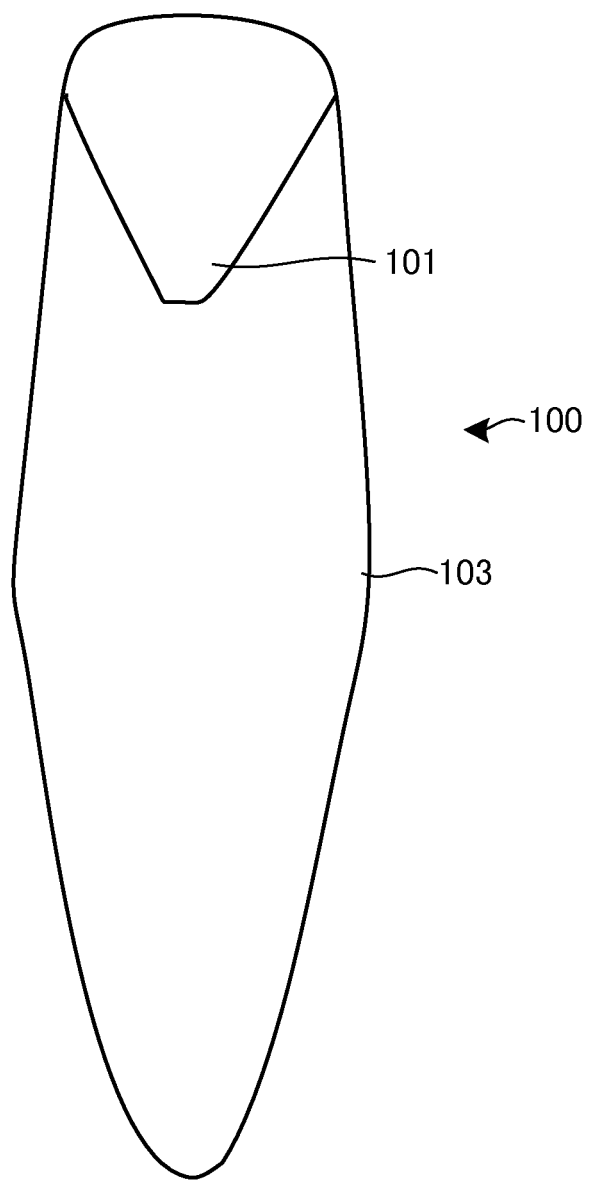
FIG. 8 is a bottom view of the drainage device according to the first embodiment of the present invention.

FIG. 8 is a bottom view of the drainage device 100. When viewed from the bottom surface of the drainage device 100, the distal end portion of the hook portion 101 is bent in the direction of the body portion 103. The body portion 103 has a round abdominal side and is formed into a shape that allows the liquid 250 to easily adhere to the surface of the drainage device 100.

Figure 9:
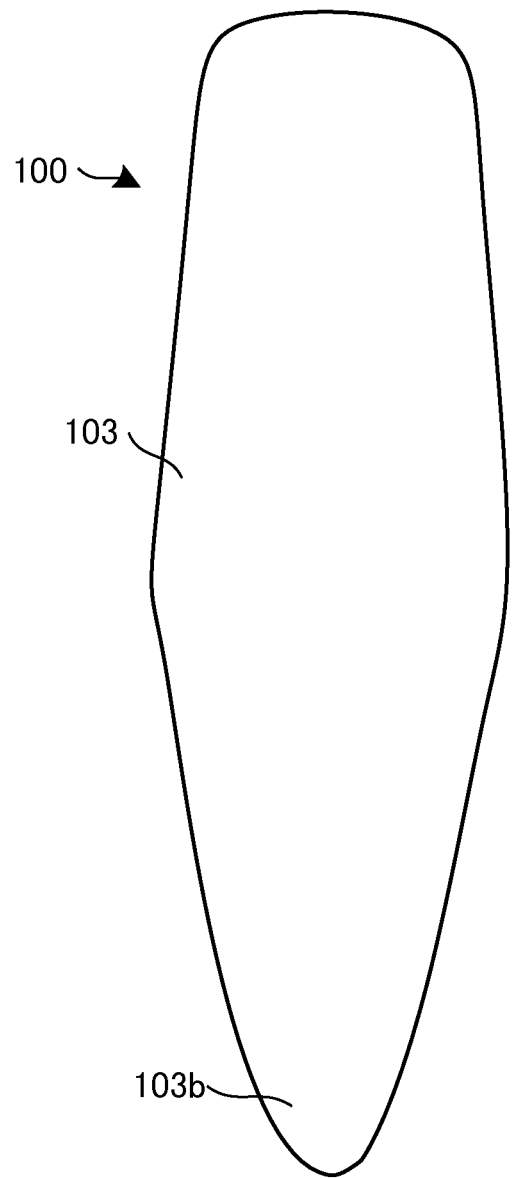
FIG. 9 is a plan view of the drainage device according to the first embodiment of the present invention.

FIG. 9 is a plan view of the drainage device 100. When viewed from a plane, the drainage device 100 has the thickest portion at the body portion 103 and is tapered toward the tail portion 103b.

The drainage device 100 may be formed from a material that can be repeatedly used by being sterilized by boiling disinfection or the like. In this case, the drainage device 100 is desirably formed by using a material which can be molded, e.g., a metal such as silver or stainless steel or silicone. On the other hand, the drainage device 100 may be of a disposable type that is discarded after one use. In this case, it is possible to use soft materials such as polyvinyl chloride (PVC), silicone rubber, various types of thermoplastic elastomer (TPE), and soft polypropylene (PP) and hard materials such as polypropylene, high-density polyethylene, and polyethylene terephthalate (PET). In any case, at least the surface of the abdominal side of the drainage device 100 is desirably formed by using a material having high wettability that can maintain a high drainage efficiency.

With the above arrangement, the drainage device according to this embodiment discharges the liquid retained in the palpebral fissure by guiding the liquid from the distal end portion of the hook portion hooked on the palpebral fissure or medical drape and making the liquid run along the body portion. It is therefore possible to easily use the drainage device according to the embodiment without using any aspirator and to easily discharge a liquid without damaging the conjunctiva and the like.

Second Embodiment

Figure 10:
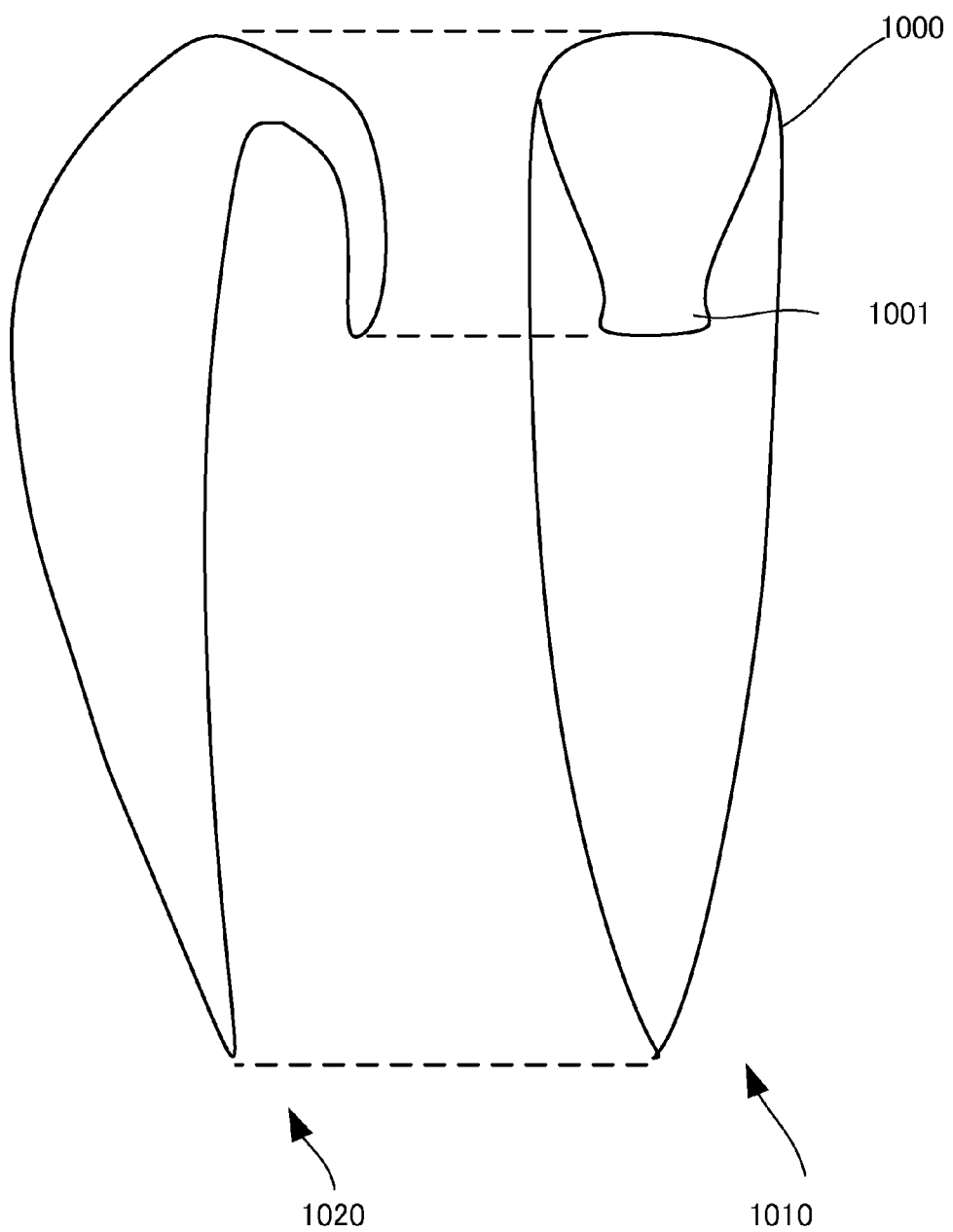
FIG. 10 is a bottom view of a drainage device according to the second embodiment of the present invention.

A drainage device 1000 as the second embodiment of the present invention will be described with reference to FIG. 10. FIG. 10 is a view showing the arrangement of the drainage device 1000 according to this embodiment. A hook portion 1001 of the drainage device 1000 which is bent into a hook has a distal end portion formed into a spatula shape (lamina shape). Reference numeral 1010 denotes a state of the drainage device 1000 viewed from the bottom surface; and 1020, a state of the drainage device 1000 viewed from the right side surface.

As compared with the drainage device 100 of the first embodiment, the hook portion 1001 has a larger area that comes into contact with the lid margin when being hooked on it, and hence is more stably placed on the lid margin. In addition, the hook portion 1001 is formed into a spatula shape to have a larger area that comes into contact with a liquid than the drainage device 100 of the first embodiment. This makes it possible to ensure a wider liquid flow path. In addition, it is possible to guide a larger amount of liquid to the body portion.

With the above arrangement, the drainage device according to this embodiment can be more stably hooked on the lid margin regardless of the installation position because the distal end portion of the hook portion is formed into a spatula shape. In addition, since the distal end portion of the hook portion is formed into a spatula shape, the drainage device can discharge a larger amount of liquid.

Third Embodiment

Figure 11:
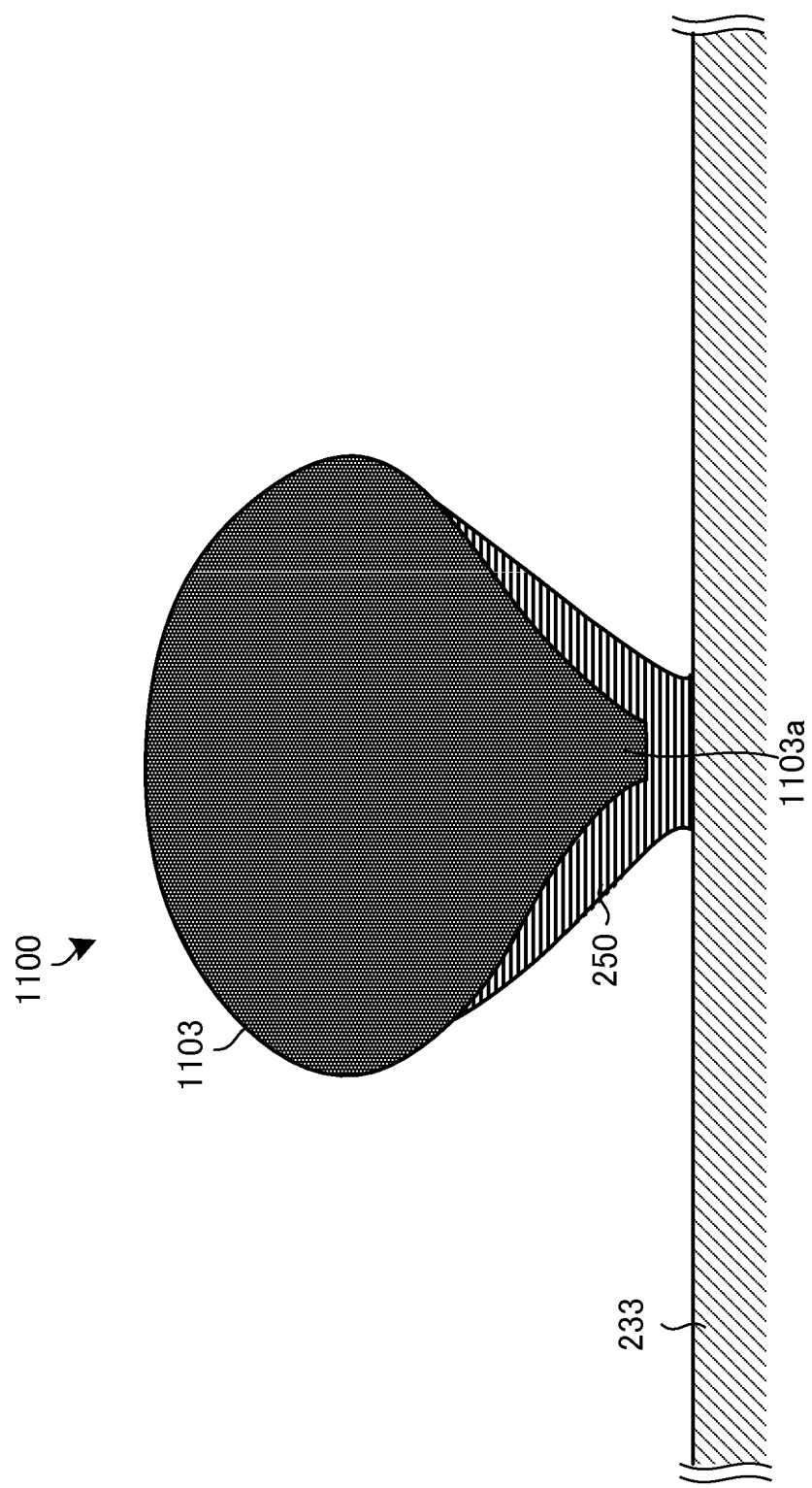
FIG. 11 is a sectional view showing a state of use of a drainage device according to the third embodiment of the present invention.

A drainage device 1100 as the third embodiment of the present invention be described with reference to FIG. 11. FIG. 11 is a sectional view of the drainage device 1100 according to this embodiment when viewed from the lid margin side.

As shown in FIG. 11, an abdominal portion 1103a of a body portion 1103 extending from a hook portion (not shown) is formed to have an almost V-shaped cross-section then viewed from the lid margin side.

Referring to FIG. 11, the surface of the abdominal portion 1103a of the body portion 1103 is not in contact with a lid margin 233, and the gap formed between the abdominal portion 1103a and the lid margin 233 functions as a capillary tube. A liquid 250 descends in the gap due to capillary action.

The abdominal portion 1103a is not in contact with the lid margin 233 and has an arcuated (concave) surface shape. This forms a large liquid flow path. Note that the drainage device 1100 may be placed so as to bring the abdominal portion of the body portion 1103 into contact with the lid margin 233.

With the above arrangement, the drainage device 1100 according to this embodiment can easily discharge a liquid because the surface of the abdominal portion 1103a of the body portion 1103 is formed into an almost V shape.

Fourth Embodiment

Figure 12:
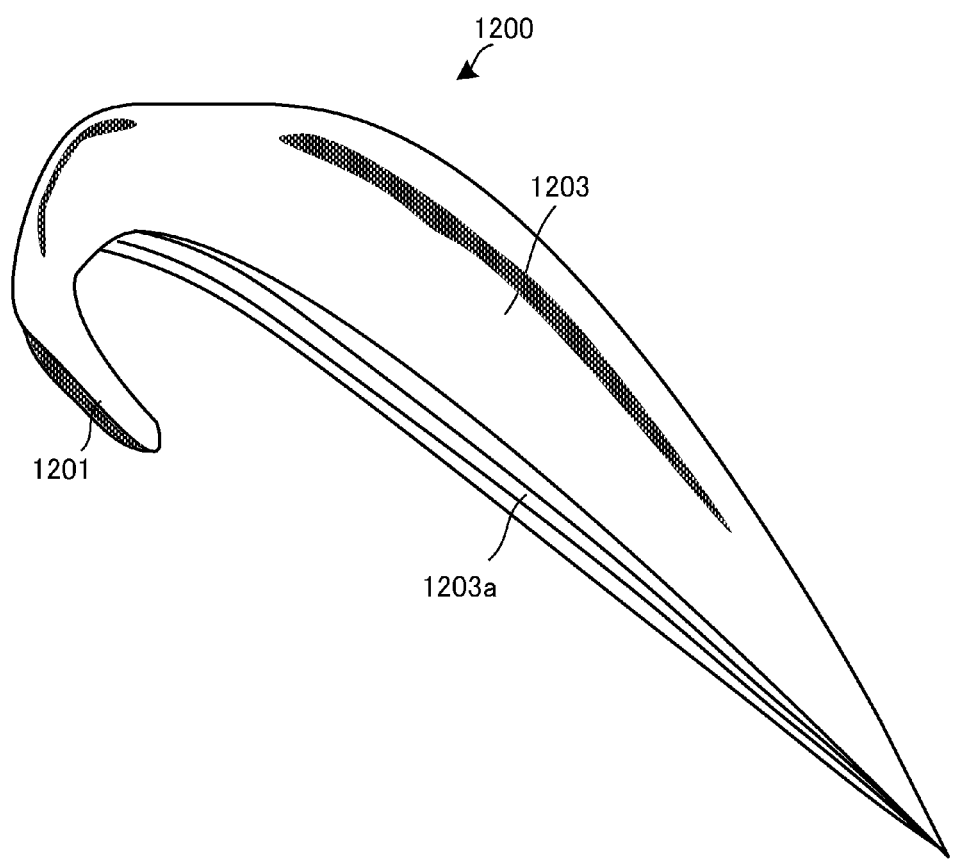
FIG. 12 is a view showing the arrangement of a drainage device according to the fourth embodiment of the present invention.

A drainage device 1200 according to the fourth embodiment of the present invention will be described with reference to FIG. 12. FIG. 12 is a perspective view showing the arrangement of the drainage device 1200 according to this embodiment. The drainage device 1200 includes a concave portion 1203a on the abdominal side of a body portion 1203, and has a concave groove extending from the base of a hook portion 1201 to the tail portion.

Figure 13:
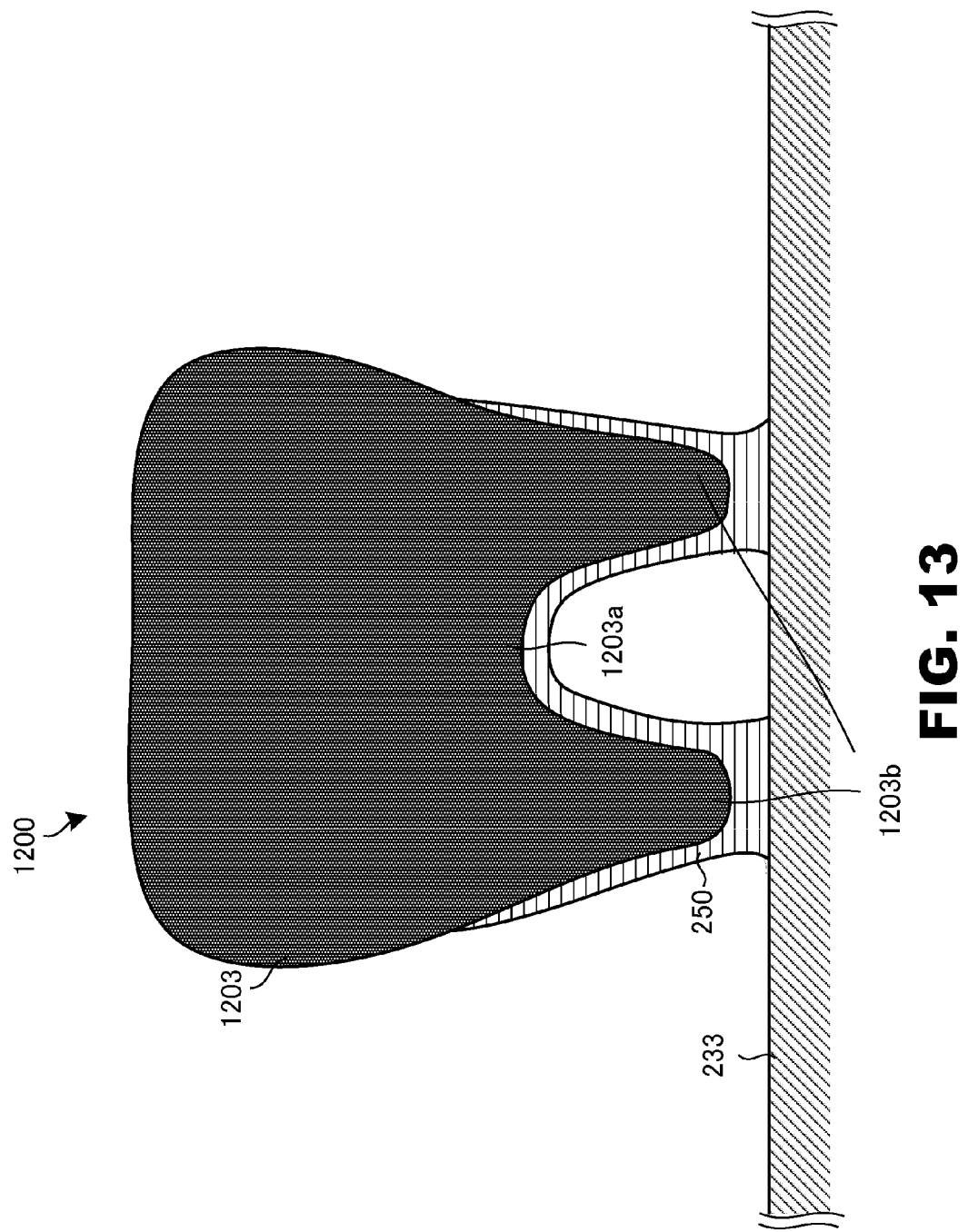
FIG. 13 is a sectional view showing a state of use of the drainage device according to the fourth embodiment of the present invention.

FIG. 13 is a sectional view showing a state of use of the drainage device 1200 according to this embodiment. As shown in FIG. 13, the drainage device 1200 includes the concave portion 1203a and convex portions 1203b on the abdominal side of the body portion 1203.

The concave portion 1203a is formed by notching a middle portion of the abdominal side surface of the body portion 1203 from the base of the hook portion to the tail portion. The pair of convex portions 1203b are formed on the two sides of the concave portion 1203a. Forming the concave portion 1203a and the convex portions 1203b increases the surface area of the body portion 1203 as compared with the drainage device 100 of the first embodiment. This makes it possible to ensure a larger flow path for a liquid 250.

With the above arrangement, the drainage device 1200 according to this embodiment discharges the liquid guided from the distal end portion of the hooked hook portion by making the liquid run along the uneven surface of the body portion. The drainage device 1200 according to this embodiment can easily discharge a larger amount of liquid without using any aspirator.

Fifth Embodiment

Figure 14:
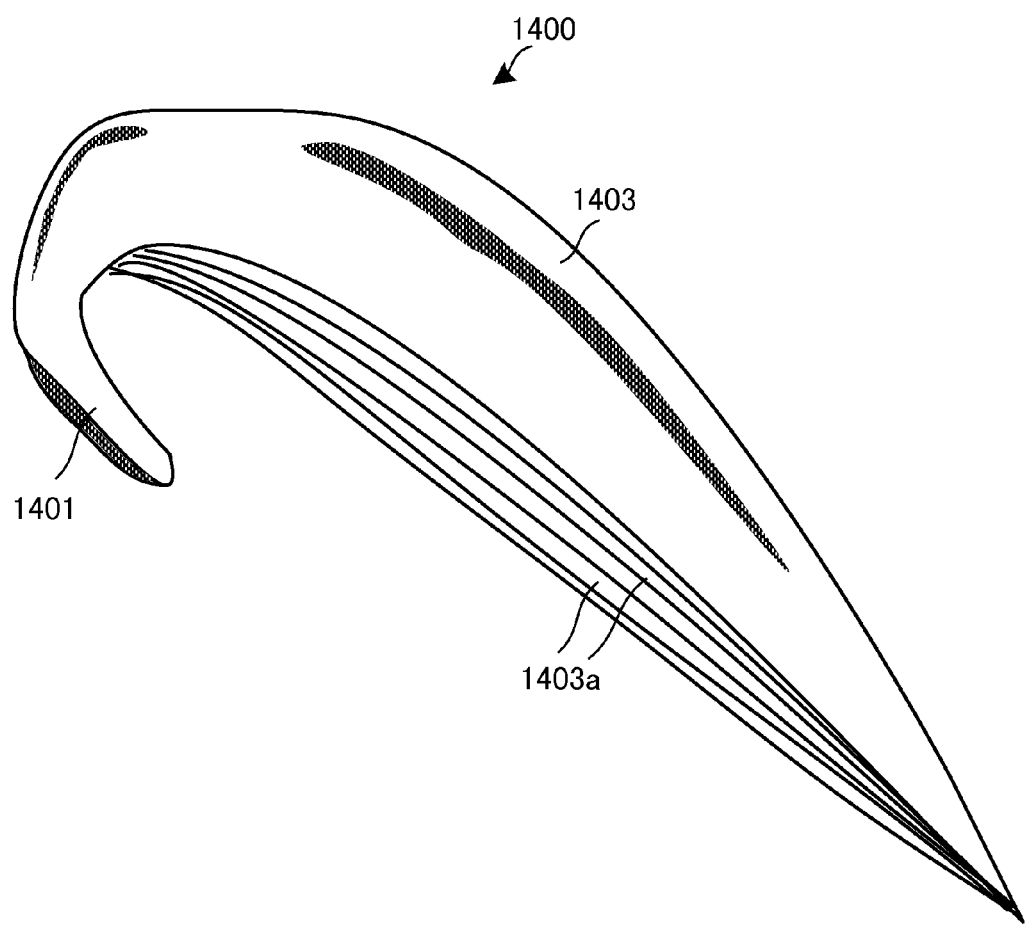
FIG. 14 is a perspective view showing the arrangement of a drainage device according to the fifth embodiment of the present invention.

A drainage device 1400 according to the fifth embodiment of the present invention will be described with reference to FIG. 14. FIG. 14 is a perspective view showing the arrangement of the drainage device 1400 according to this embodiment. The drainage device 1400 includes a plurality of concave portions 1403a each having a groove-like shape formed on the abdominal side of a body portion 1403 so as to extend from the base of a hook portion 1401 to the tail portion.

Figure 15:
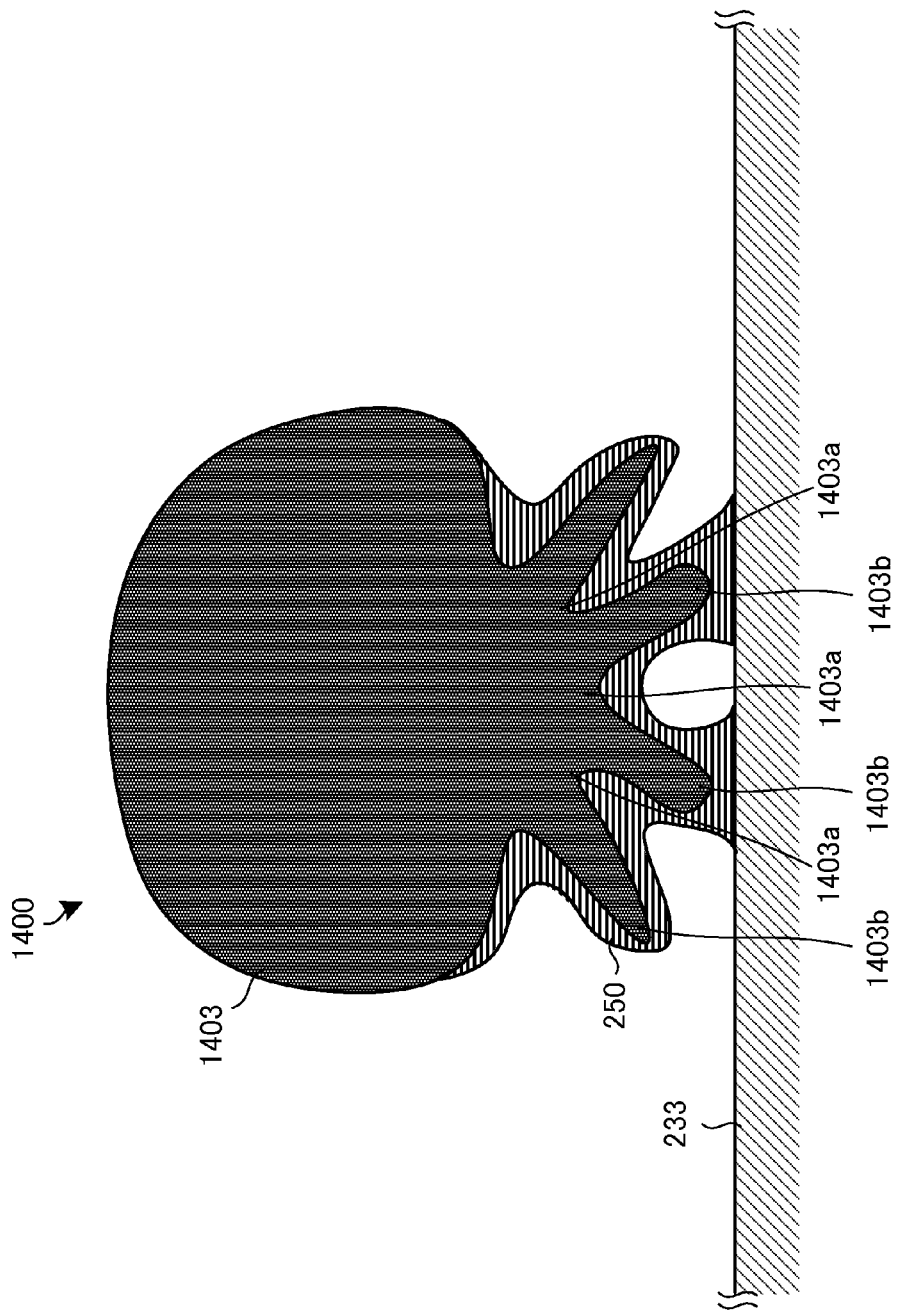
FIG. 15 is a sectional view showing a state of use of the drainage device according to the fifth embodiment of the present invention.

FIG. 15 is a cross-sectional view taken along a plane perpendicular to an axis and viewed from the lid margin side. As shown in FIG. 15, the drainage device 1400 includes a plurality of concave portions 1403a and a plurality of convex portions 1403b on the abdominal side of the body portion 1403. The body portion 1403 therefore has an almost polygonal sectional shape formed into folds by notching a plurality of concave and convex portions.

The concave portions 1403a are notched on the abdominal side of the body portion 1403 so as to extend from the bent portion of the hook portion to the tail portion. The convex portions 1403b and the concave portions 1403a are alternatively formed.

Forming the plurality of concave portions 1403a and the plurality of convex portions 1403b on the body portion 1403 of the drainage device 1400 can ensure a wider flow path for the liquid 250 as compared with the drainage device 100 of the first embodiment.

With the above arrangement, the drainage device 1400 according to this embodiment discharges the liquid guided from the distal end portion of the hooked hook portion by making the liquid run along the surface of the body portion having the plurality of concave and convex portions. That is, the drainage device according to this embodiment can easily discharge a large amount of liquid without using any aspirator.

Sixth Embodiment

Figure 16:
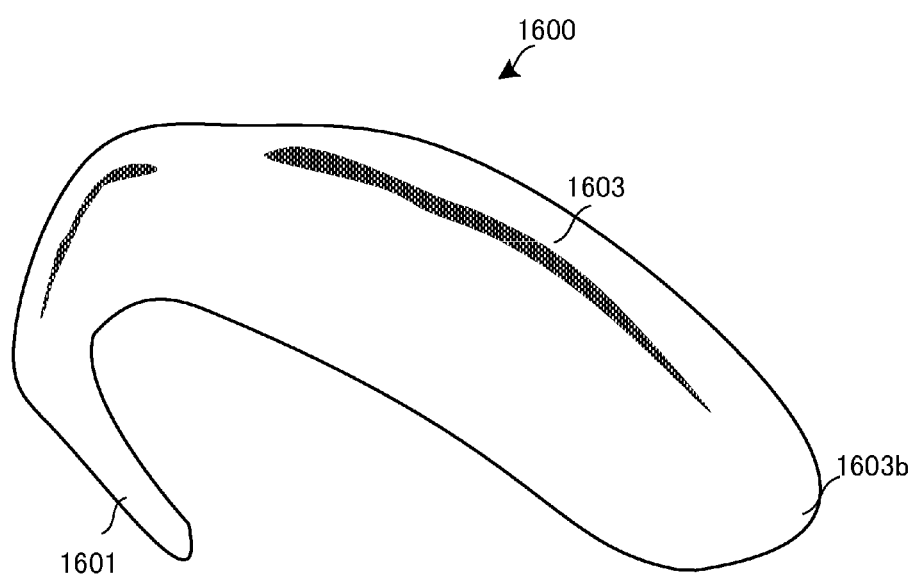
FIG. 16 is a perspective view showing the arrangement of a drainage device according to the sixth embodiment of the present invention.

A drainage device 1600 according to the sixth embodiment of the present invention will be described with reference to FIG. 16. FIG. 16 is a perspective view showing the arrangement of the drainage device 1600 according to this embodiment.

As shown in FIG. 16, the drainage device 1600 includes a hook portion 1601 and a body portion 1603 having a shorter tail portion 1603b. That is, the drainage device 1600 differs from the drainage device 100 shown in FIG. 2A in that the tail portion 1603b of the body portion 1603 is shorter and has a round shape.

Figure 17:
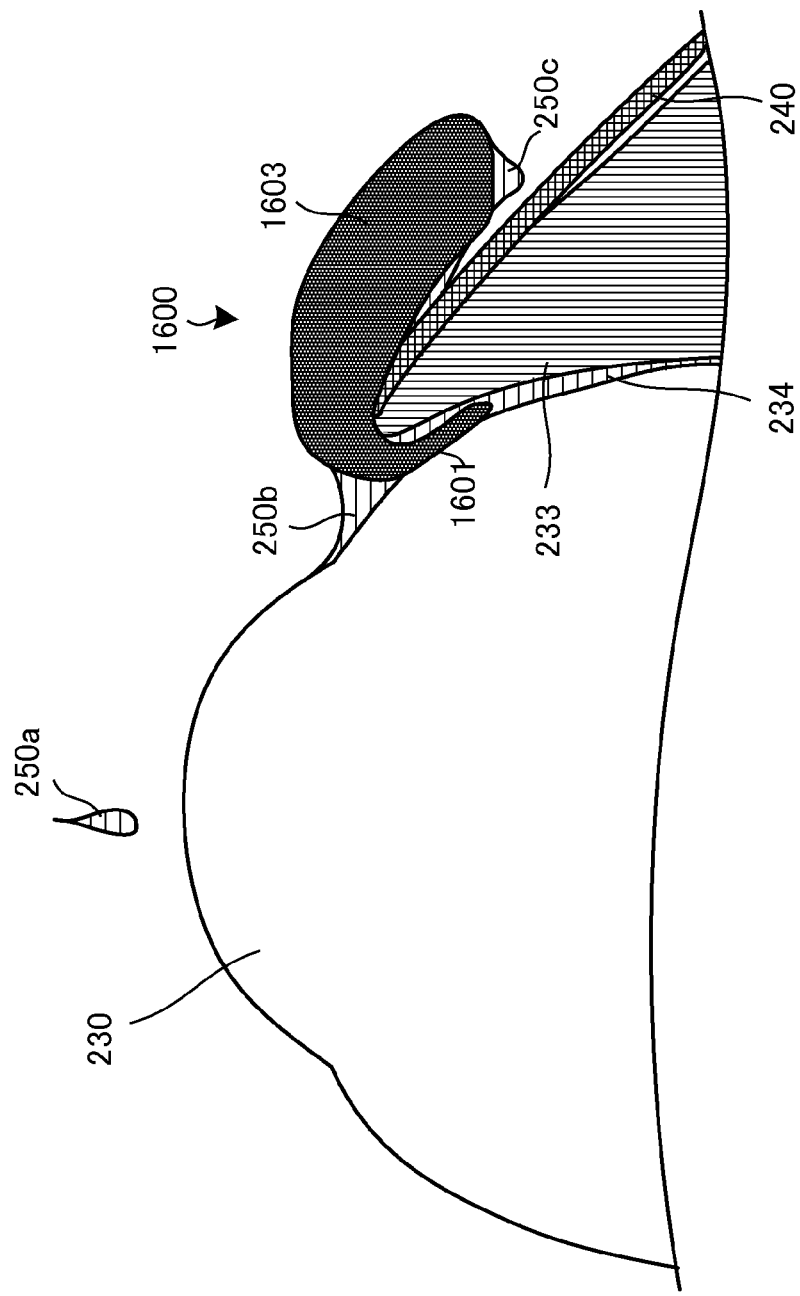
FIG. 17 is a sectional view showing a state of use of the drainage device according to the sixth embodiment of the present invention.

FIG. 17 is a sectional view of the lid margin on which the drainage device 1600 according to this embodiment is placed and a peripheral portion of the lid margin, taken along a plane passing through the medial ocular angle and the lateral ocular angle.

Although the body portion 1603 is shorter than that of the drainage device 100, a constant amount of liquid 250 runs along the hook portion 1601. This device also discharges a constant amount of liquid 250 from the tail portion by making the liquid run along the surface of the body portion 1603. That is, the amount of liquid 250 discharged from the palpebral fissure by the drainage device 1600 is almost equal to that by the drainage device 100 even if the end portion of the body portion 1603 is shorter than that of the drainage device 100.

With the above arrangement, the drainage device according to this embodiment can be easily used and can easily discharge a liquid without using any aspirator.

Seventh Embodiment

Figure 18:
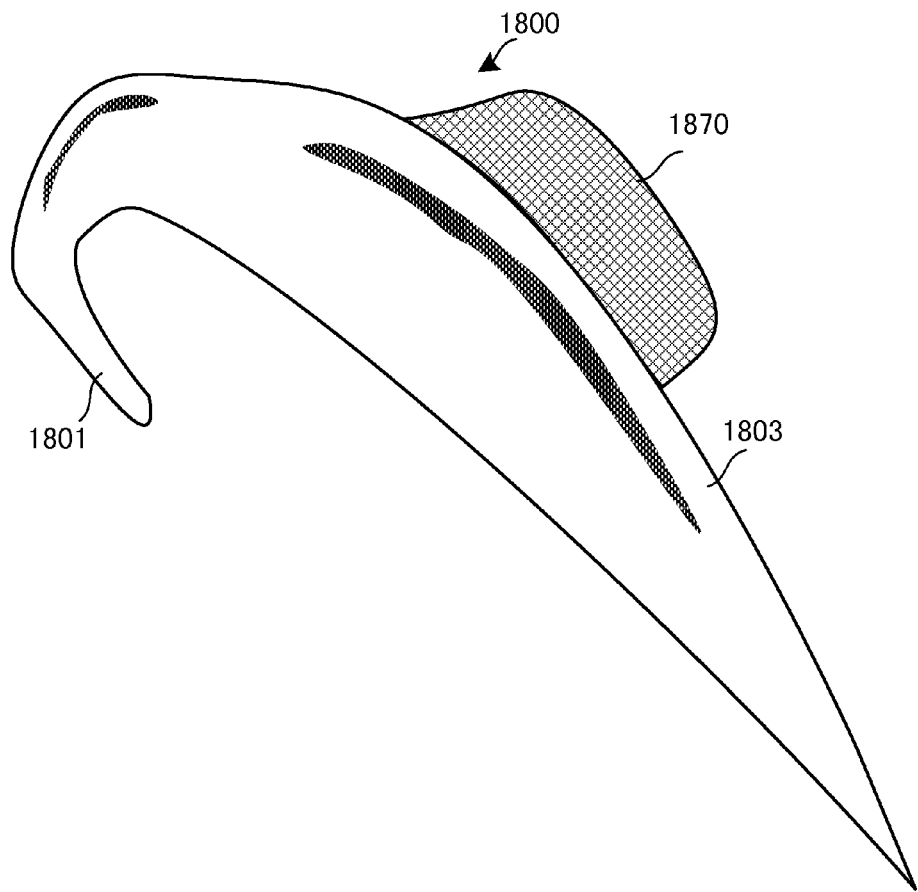
FIG. 18 is a perspective view showing the arrangement of a drainage device according to the seventh embodiment of the present invention.

A drainage device 1800 according to the seventh embodiment of the present invention will be described with reference to FIG. 18. FIG. 18 is a perspective view showing the arrangement of the drainage device 1800 according to this embodiment. The drainage device 1800 differs from the drainage device 100 shown in FIGS. 2A and 2B in that a body portion 1803 has a grip portion 1870 on its rear surface.

The distal end portion of a hook portion 1801 is tapered. The body portion 1803 is spindle-shaped. The tail portion is tapered toward its end.

Forming the grip portion 1870 on the rear surface of the body portion 1803 allows the practitioner to very easily hold the drainage device 1800. The grip portion 1870 is not limited to the shape shown in FIG. 18 and may have any shape as long as it is suitable for gripping at the time of use. The formation position of the grip portion 1870 is not limited to that shown in FIG. 18 and may be any position which is suitable for gripping at the time of use and does not interfere with the progression of surgery.

With the above arrangement, in addition to the effects of the first embodiment, the drainage device according to this embodiment has the effect of allowing easier gripping when it is placed on the lid margin or removed from it.

Eighth Embodiment

Figure 19:
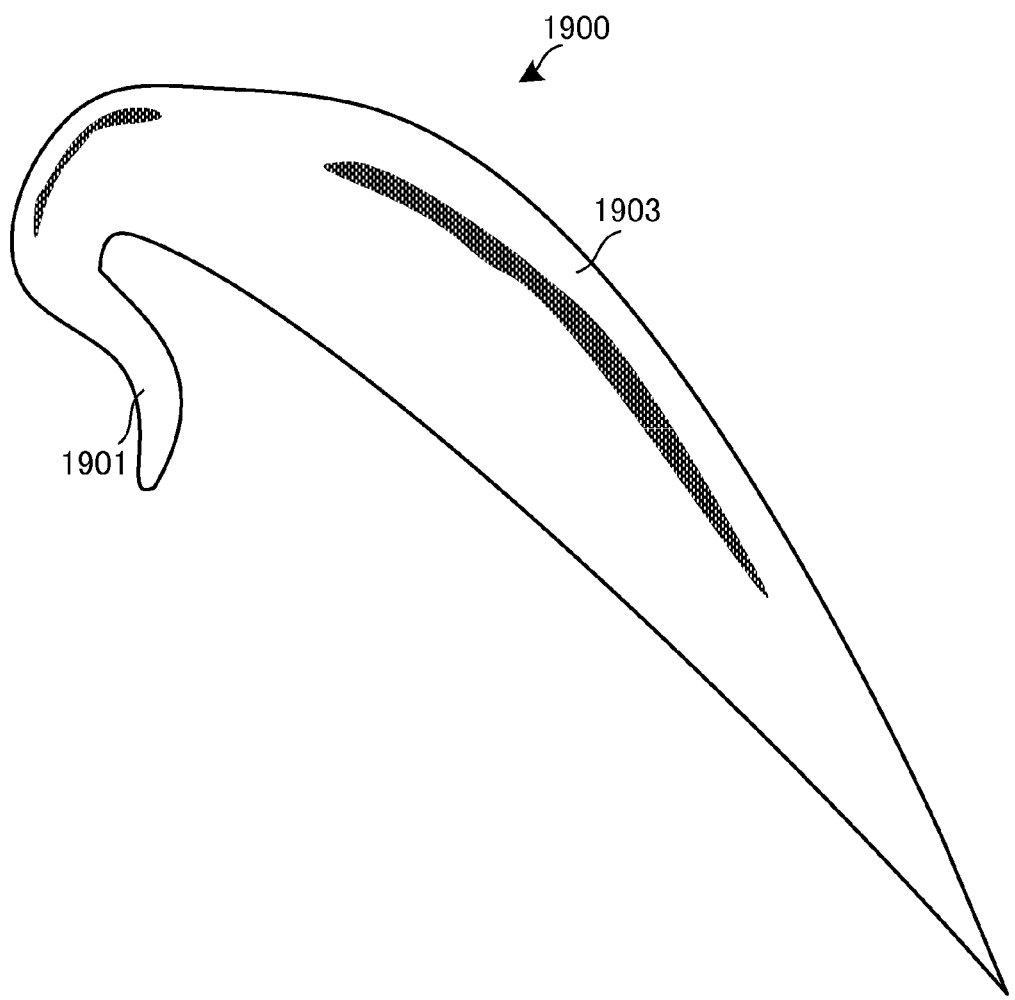
FIG. 19 is a perspective view showing the arrangement of a drainage device according to the eighth embodiment of the present invention.

A drainage device 1900 as the eighth embodiment of the present invention will be described with reference to FIG. 19. FIG. 19 is a perspective view showing the arrangement of the drainage device 1900 according to this embodiment. The drainage device 1900 differs from the drainage device 100 shown in FIGS. 2A and 2B in that the distal end portion of a hook portion 1901 is bent into a convex arcuated shape relative to a body portion 1903.

Figure 20:
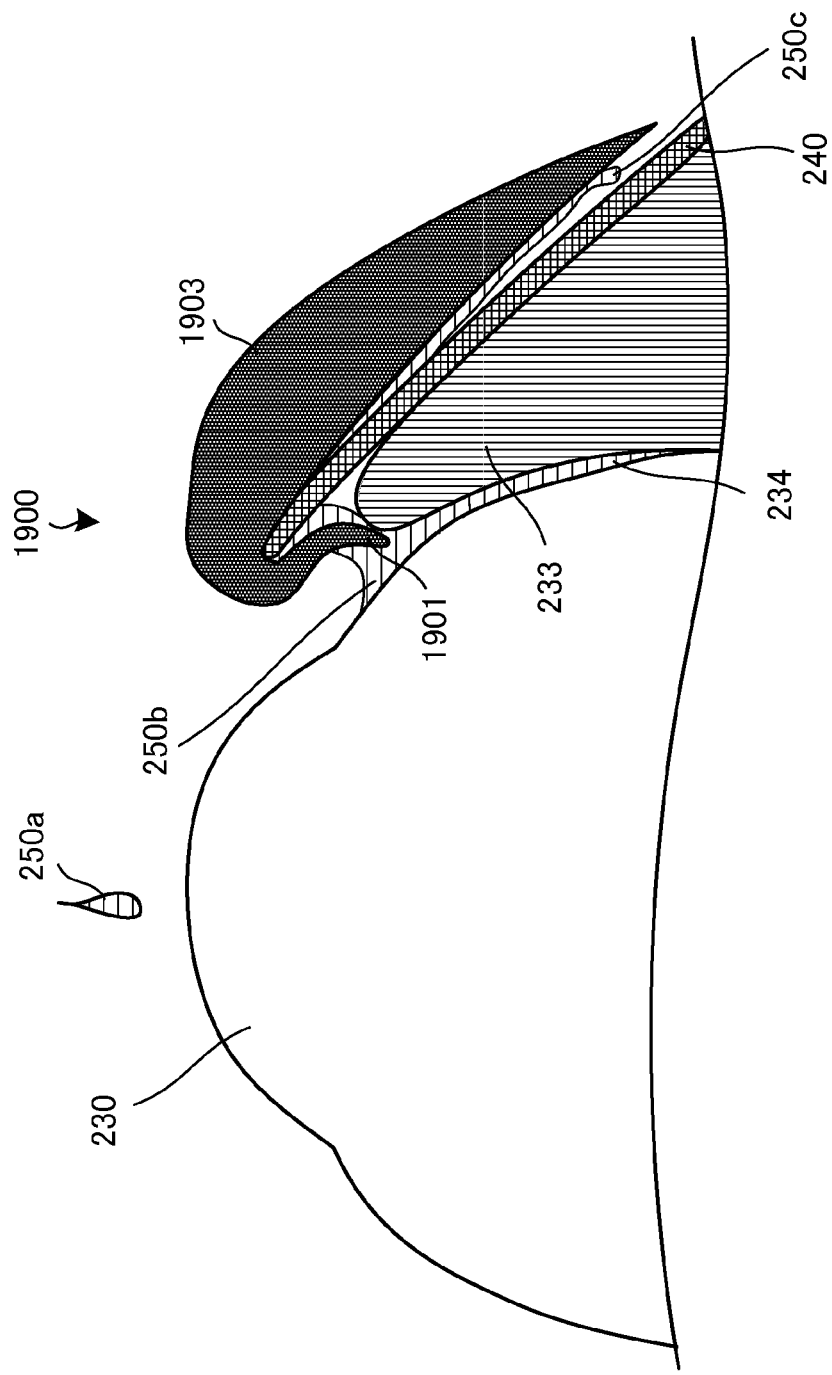
FIG. 20 is a sectional view showing a state of use of the drainage device according to the eighth embodiment of the present invention.

FIG. 20 is a sectional view showing a state of use of the drainage device 1900 according to this embodiment, and is a sectional view of the palpebral fissure on which the drainage device 1900 is placed and a peripheral portion of the palpebral fissure, taken along a plane passing through the medial ocular angle and the lateral ocular angle.

The distal end portion of hook portion 1901 is bent in a direction away from the body portion 1903. With this arrangement, when the hook portion is placed on an edge of a medical drape 240, the distal end portion of the hook portion 1901 comes closer to the liquid level of 250b in the palpebral fissure than the hook portion 101 of the drainage device 100 shown in FIG. 2B. This makes it easy to cause capillary action between the distal end portion of the hook portion 1901, the medical drape 240, and the liquid 250, and hence can more efficiently discharge the liquid retained in the palpebral fissure.

With the above arrangement, the drainage device according to this embodiment can effectively discharge a liquid from the palpebral fissure even if the drainage device is placed on the medical drape instead of the lid margin.

Ninth Embodiment

Figure 21:
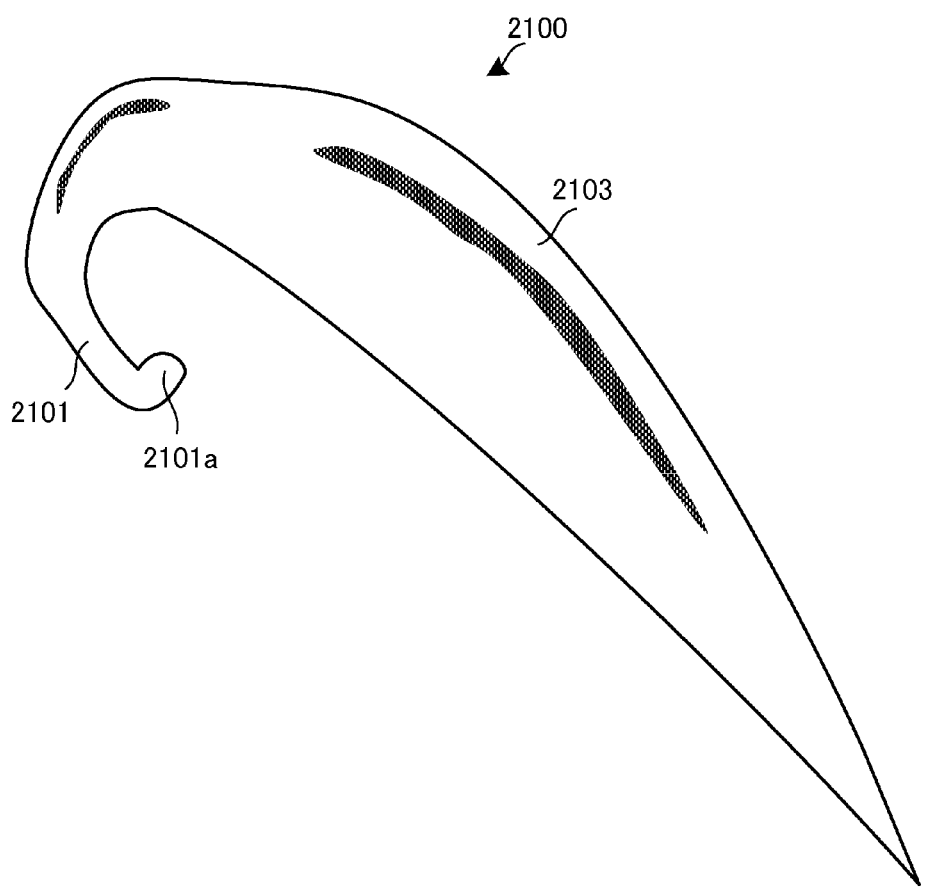
FIG. 21 is a perspective view showing the arrangement of a drainage device according to the ninth embodiment of the present invention.

A drainage device 2100 according to the ninth embodiment of the present invention will be described with reference to FIG. 21. FIG. 21 is a perspective view showing the arrangement of the drainage device 2100 according to this embodiment. This drainage device differs from the drainage device 100 shown in FIGS. 2A and 2B in that the distal end of a hook portion 2101 of the drainage device 2100 is formed to include a convex portion 2101a protruding toward a body portion 2103.

Figure 22:
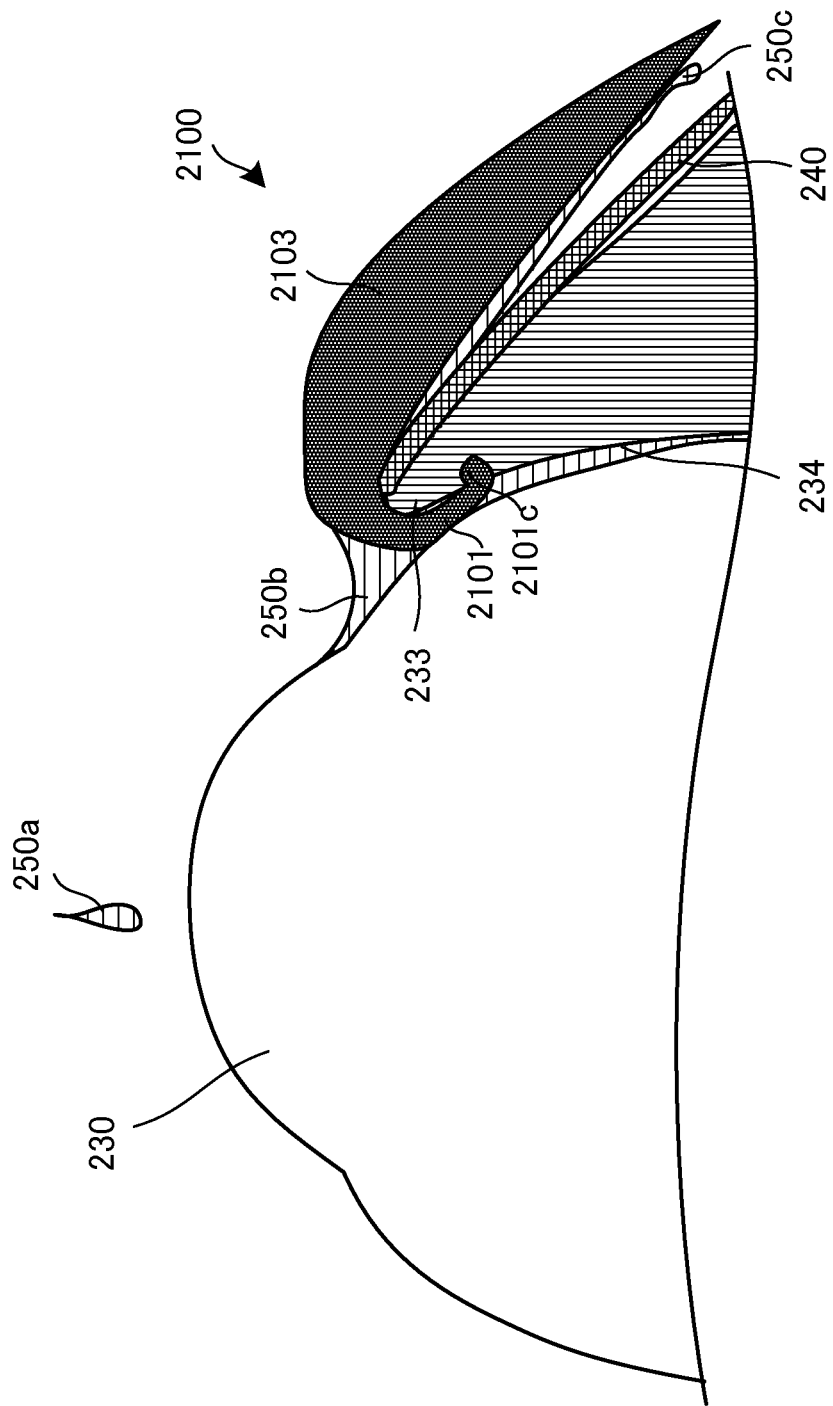
FIG. 22 is a sectional view showing a state of use of the drainage device according to the ninth embodiment of the present invention.

FIG. 22 is a sectional view showing a state of use of the drainage device 2100 according to this embodiment, and is a sectional view of the palpebral fissure on which the drainage device 2100 is placed and a peripheral portion of the palpebral fissure, taken along a plane passing through the medial ocular angle and the lateral ocular angle. When the drainage device 2100 is placed on a lid margin 233, the convex portion 2101a protruding toward the body portion 2103 is hooked on the lid margin 233 or a conjunctival sac 234. This makes it more hard for the hook portion 2101 to slip off as compared with the hook portion 101 of the drainage device 100 shown in FIG. 2A. That is, this makes it possible to prevent the drainage device 2100 from slipping off the lid margin 233 due to vibrations and the like during surgery.

With the above arrangement, in addition to the effects of the first embodiment, the drainage device according to the ninth embodiment has the effect of making it hard for the drainage device to slip off during surgery.

10th Embodiment

Figure 23A:
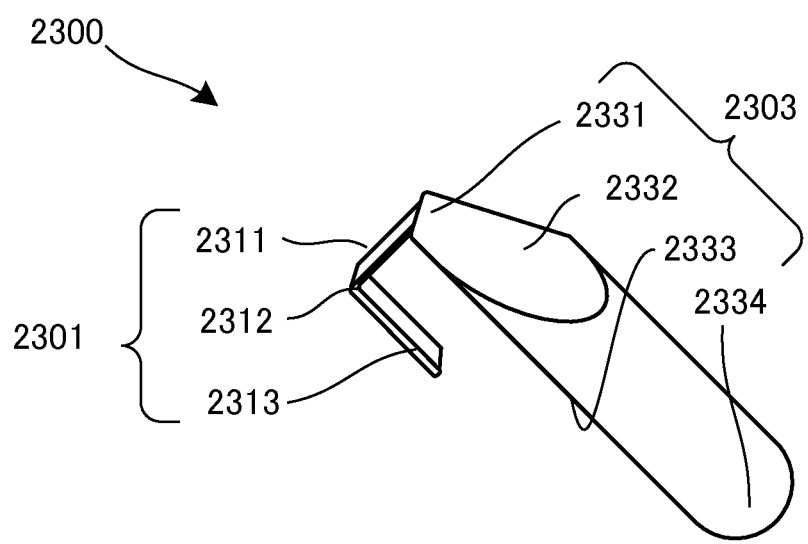
FIG. 23A is a perspective view showing the arrangement of a drainage device according to the 10th embodiment of the present invention.

A drainage device 2300 according to the 10th embodiment of the present invention will be described with reference to FIGS. 23A and 23B. FIG. 23A is a perspective view showing the arrangement of the drainage device 2300 according to this embodiment. The drainage device 2300 is also a drainage device for discharging the liquid retained in the palpebral fissure to the outside of the palpebral fissure. This drainage device, however, differs from the drainage device 100 shown in FIGS. 2A and 2B in that a hook portion 2301 of the drainage device 2300 extends at a right angle to the axis of a body portion 2303 and is bent at a bent portion 2312 so as to extend parallel to the axis toward a tail portion 2334 of the body portion. In addition, they differ in that the body portion 2303 is formed from an almost columnar body having a constant thickness.

The hook portion 2301 is bent into a hook (in this case, an L shape) to be hooked on the lid margin or medical drape, and comes into contact with the liquid in the palpebral fissure or the liquid overflowing from the palpebral fissure to form the start point of the liquid flow path. The hook portion 2301 has a hanging portion 2311, the bent portion 2312, and a distal end portion 2313. To hook on the palpebral fissure or medical drape, the hook portion 2301 extends from a hook connecting portion 2331 as a start point in a direction perpendicular to the axis of the body portion 2303 by 3 mm to 10 mm, and preferably 3 mm to 6 mm, bends at a right angle at the bent portion 2312, and extends toward the tail portion 2334 of the body portion 2303 by 3 mm to 10 mm, and preferably 3 mm to 6 mm. In this embodiment, the hook portion 2301 bends at an almost right angle at the bent portion 2312, and the distal end portion 2313 extends parallel to an abdominal portion 2333 of the body portion 2303. However, the present invention is not limited to this, and the hook portion 2301 may bend at an angle of 90° or more or 90° or less. That is, the hook portion 2301 may bend at an acute angle (e.g., 60°) (so as to approach the abdominal portion 2333) or bend at an obtuse angle (120°) (so as to separate from the abdominal portion 2333). Forming the distal end portion 2313 having a surface with a certain width will increase the area that comes into contact with a liquid and allows the main body to stably hook on the palpebral fissure or medical drape. The distal end portion 2313 is formed into a spatula shape (flat lamina shape) having a width smaller than that of the thickest portion of the body portion 2303.

The body portion 2303 is formed from a solid columnar body which extends from the hook connecting portion 2331 to the tail portion 2334, including the abdominal portion 2333. The body portion 2303 discharges the liquid guided by the hook portion 2301 to the outside upon making the liquid reach the surface of the tail portion 2334 by making the liquid run along the gap between the lid margin side surface of the abdominal portion 2333 and the lid margin or medical drape. Note that in this embodiment, the body portion 2303 has an almost columnar shape but is not limited to this. For example, the body portion 2303 may have a polygonal columnar shape having three or more corners. Therefore, the body portion 2303 has an almost true circular cross-section when being cut along a plane perpendicular to the axis and viewed from the lid margin side in this embodiment, but may have an elliptic, polygonal, or irregular cross-section.

The body portion 2303 includes an inclined surface 2332 which is inclined relative to the axis of the body portion and extends from the hook connecting portion 2331 toward the back side (the opposite side of the abdominal portion 2333). The inclined surface 2332 forms an acute angle with respect to the abdominal portion 2333, and the angle defined between them is preferably 30° to 60°. In addition, the inclined surface 2332 occupies about ⅓ the total length of the body portion 2303 in this embodiment. However, the present invention is not limited to this. Furthermore, the inclined surface 2332 may be a flat or curved surface. Forming the inclined surface 2332 can prevent a tool from coming into contact with the drainage device 2300 during surgery, thereby providing a more user-friendly drainage device.

Since the body portion 2303 is formed from a columnar body, the surface of the abdominal portion 2333 which faces the lid margin is formed into a curved surface. The liquid guided by the hook portion 2301 is therefore discharged to the outside of the palpebral fissure by being made to run along this curved surface.

Figure 23B:
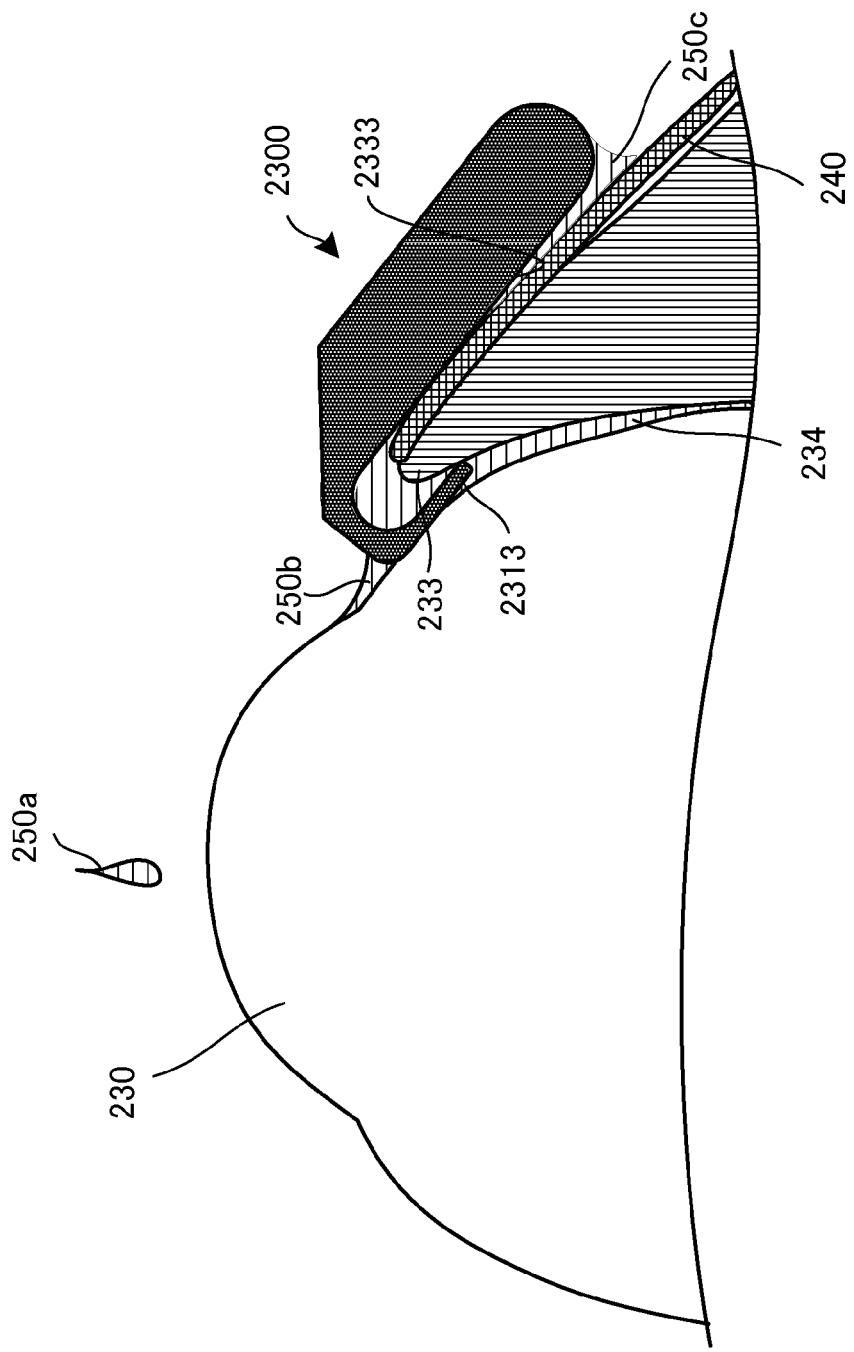
FIG. 23B is a sectional view showing a state of use of the drainage device according to the 10th embodiment of the present invention.

FIG. 23B is a sectional view of the palpebral fissure on which the drainage device 2300 is hooked and a peripheral portion of the palpebral fissure, taken along a plane passing through the medial ocular angle and the lateral ocular angle. The drainage device 2300 has a larger space formed between the distal end portion 2313 of the hook portion 2301 and the abdominal portion 2333 of the body portion 2303, and hence is more easily hooked on a lid margin 233 or a medical drape 240.

With the above arrangement, the drainage device according to this embodiment can easily and stably discharge a liquid without using any aspirator.

11th Embodiment

Figure 24A:
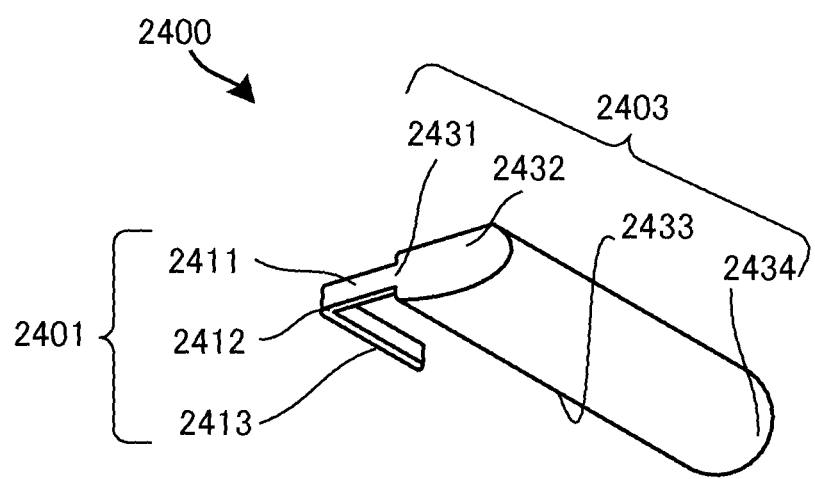
FIG. 24A is a perspective view showing the arrangement of a drainage device according to the 11th embodiment of the present invention.

A drainage device 2400 as the 11th embodiment of the present invention will be described with reference to FIGS. 24A and 24B. FIG. 24A is a perspective view showing the arrangement of the drainage device 2400 according to this embodiment. The drainage device 2400 differs from the drainage device 2300 shown in FIG. 23A in that a hook portion 2401 is formed along an inclined surface 2432 of a body portion 2403.

As shown in FIG. 24A, the drainage device 2400 includes the hook portion 2401 and the body portion 2403. The body portion 2403 is formed from a solid columnar body and includes a hook connecting portion 2431 the inclined surface 2432, an abdominal portion 2433, and a tail portion 2434.

The inclined surface 2432 is formed so as to be inclined relative to the axis of the body portion and so as to extend from the hook connecting portion 2431 toward the back side (the opposite side of the abdominal portion 2433). The inclined surface 2432 forms an acute angle with respect to the surface of the abdominal portion 2433. This angle is preferably 30° to 60°. In addition, the inclined surface 2432 occupies about ⅓ the total length of the body portion 2403 in this embodiment. However, the present invention is not limited to this. Furthermore, the inclined surface 2432 may be a flat or curved surface. Forming the inclined surface 2432 can prevent a tool from coming into contact with the drainage device 2400 during surgery, thereby providing a more user-friendly drainage device.

The hook portion 2401 is bent into a hook (in this case, a V shape) to be hooked on the lid margin or medical drape, and comes into contact with the liquid in the palpebral fissure or the liquid overflowing from the palpebral fissure to form the start point of the liquid flow path. The hook portion 2401 has a bent portion 2411, the hanging portion 2412, and a distal end portion 2413. To hook on the palpebral fissure or medical drape, the hook portion 2401 extends from a hook connecting portion 2431 as a start point in a direction at an obtuse angle (120°) with respect to the axis of the body portion 2403 by 3 mm to 10 mm, and preferably 3 mm to 6 mm, bends at an acute angle at the bent portion 2412, and extends toward the tail portion 2434 of the body portion 2403 by 3 mm to 10 mm, and preferably 3 mm to 10 mm. In this embodiment, the hook portion 2401 bends at an angle of about 60° at the bent portion 2412, and the distal end portion 2413 extends parallel to an abdominal portion 2433 of the body portion 2403. However, the present invention is not limited to this, and the hook portion 2401 may bend at an angle of 60° or more or 60° or less. That is, the hook portion 2401 may bend at an acute angle (e.g., 45°) (so as to approach the abdominal portion 2433) or bend at a right angle (90°) (so as to separate from the abdominal portion 2420). Forming the distal end portion 2413 having a surface with a certain width will increase the area that comes into contact with a liquid and allows the main body to stably hook on the palpebral fissure or medical drape. The distal end portion 2413 is formed into a spatula shape (flat lamina shape) having a width smaller than that of the thickest portion of the body portion 2403.

Note that in this embodiment, the body portion 2403 has a columnar shape with a D-shaped section. However, the present invention is not limited to this. For example, this body portion may have a polygonal columnar shape having three or more corners.

Figure 24B:
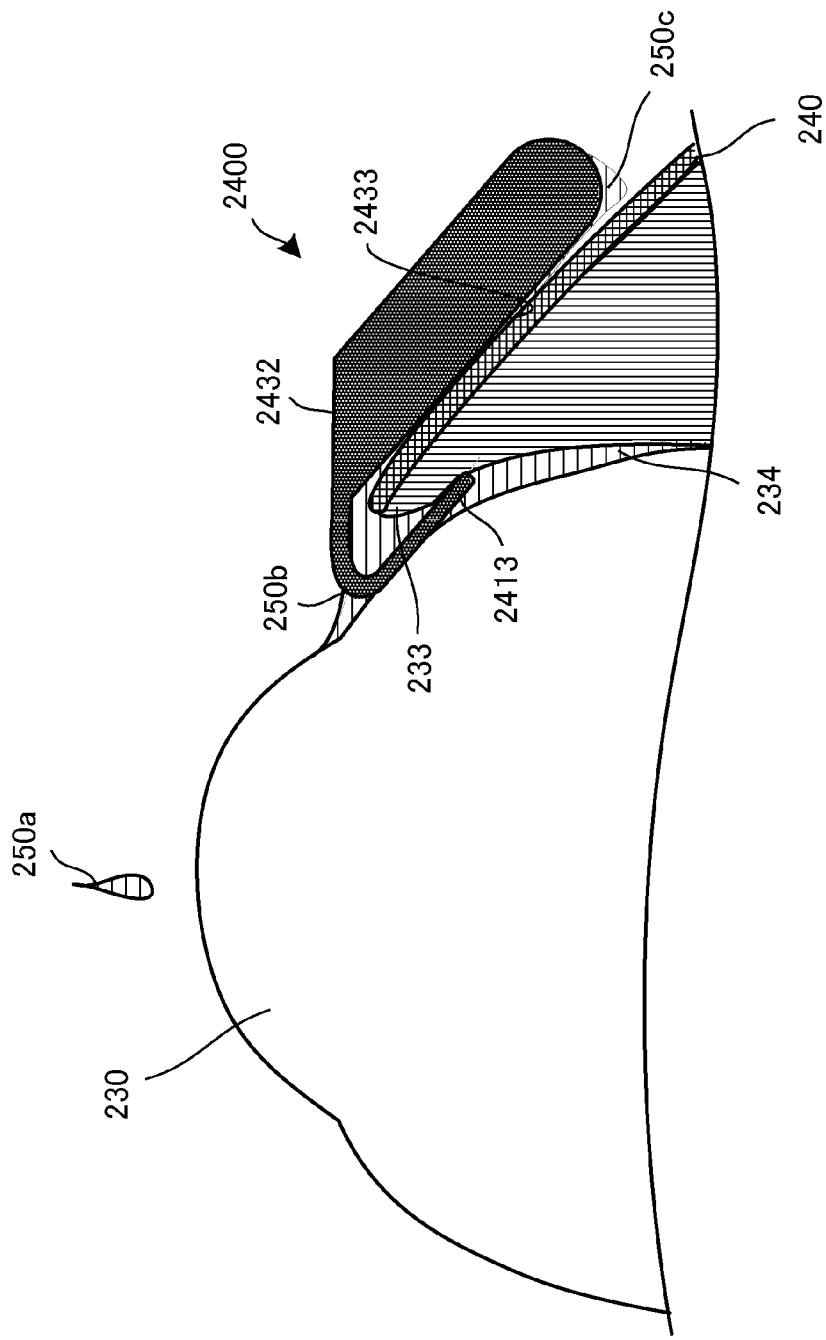
FIG. 24B is a sectional view showing a state of use of the drainage device according to the 11th embodiment of the present invention.

FIG. 24B is a sectional view of the palpebral fissure on which the drainage device 2400 is hooked and a peripheral portion of the palpebral fissure, taken along a plane passing through the medial ocular angle and the lateral ocular angle. The distal end portion 2413 of the hook portion 2401 is hooked on the conjunctival sac 234.

The drainage device 2400 has a space formed larger (deeper) between the distal end portion 2413 of the hook portion 2401 and the abdominal portion 2433 of the body portion 2403 to further facilitate hooking on a lid margin 233 or a medical drape 240.

With the above arrangement, the drainage device according to this embodiment can easily and stably discharge a liquid without using any aspirator.

12th Embodiment

Figure 25A:
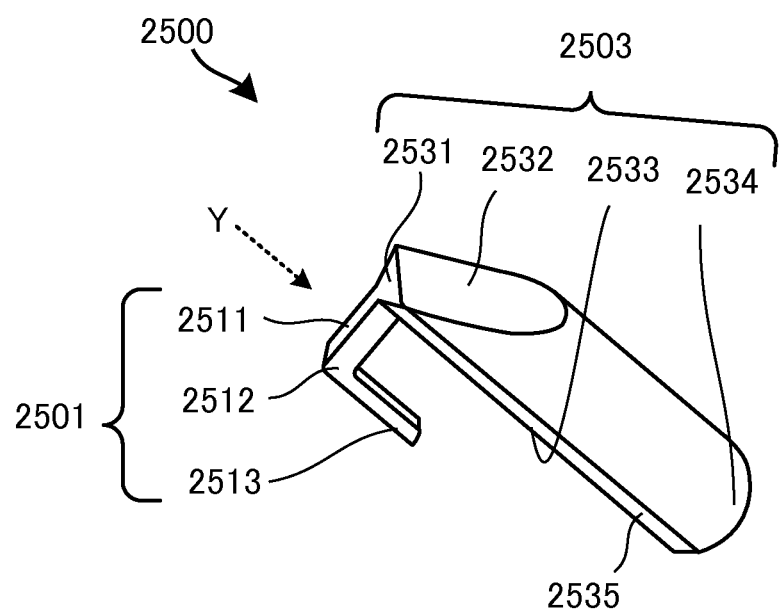
FIG. 25A is a perspective view showing the arrangement of a drainage device according to the 12th embodiment of the present invention.

A drainage device 2500 as the 12th embodiment of the present invention will be described with reference to FIGS. 25A to 25C. FIG. 25A is a perspective view showing the arrangement of the drainage device 2500 according to this embodiment. The drainage device 2500 is also a drainage device for discharging the liquid retained in the palpebral fissure to the outside of the palpebral fissure. However, this drainage device differs from the drainage device 2300 shown in FIG. 23 in that a hook portion 2501 of the drainage device 2500 is small in lateral width when viewed from the Y direction of a hanging portion 2511 extending at a right angle with respect to the axis of a body portion 2503 and is large in depth when viewed from the Y direction. They also differ in that the body portion 2503 has inclined surfaces 2535 extending from the surface of an abdominal portion 2533 which faces the lid margin toward the rear side.

As shown in FIG. 25A, the drainage device 2500 includes the hook portion 2501 and the body portion 2503.

The hook portion 2501 is bent into a hook (in this case, an L shape) to be hooked on the lid margin or medical drape, and comes into contact with the liquid in the palpebral fissure or the liquid overflowing from the palpebral fissure to form the start point of the liquid flow path. The hook portion 2501 has a hanging portion 2511, the bent portion 2512, and a distal end portion 2513. To hook on the lid margin or medical drape, the hook portion 2501 extends from a hook connecting portion 2531 as a start point in a direction perpendicular to the axis of the body portion 2503 by 3 mm to 10 mm, and preferably 3 mm to 6 mm, bends at a right angle at the bent portion 2512, and extends toward the tail portion 2534 of the body portion 2503 by 3 mm to 10 mm, and preferably 3 mm to 6 mm. In this embodiment, the hook portion 2501 bends at an almost right angle at the bent portion 2512, and the distal end portion 2513 extends parallel to an abdominal portion 2533 of the body portion 2503. However, the present invention is not limited to this, and the hook portion 2501 may bend at an angle of 60° or more or 60° or less. That is, the hook portion 2501 may bend at an acute angle (e.g., 45°) (so as to approach the abdominal portion 2533) or bend at an obtuse angle (100°) (so as to separate from the abdominal portion 2533). Forming the distal end portion 2513 having a surface with a certain width will increase the area that comes into contact with a liquid and allows the main body to stably hook on the lid margin or medical drape. The distal end portion 2513 is formed into a spatula shape (flat lamina shape) having a width smaller than that of the thickest portion of the body portion 2503.

The body portion 2503 is formed from a solid columnar body and includes a hood connecting portion 2531, an inclined surface 2532, the abdominal portion 2533, and the tail portion 2534. The body portion 2503 in this embodiment has a form obtained by bonding the opposing bottom surfaces of a columnar body having a D-shaped section and a columnar body having a trapezoidal section. The body portion 2503 is formed such that the columnar body extending from the hood connecting portion 2531 to the tail portion 2534 has a uniform thickness. As shown in FIG. 25C, therefore, a cross-sectional shape of the body portion 2503, taken along a plane perpendicular to the axis, shows that the abdominal portion 2533 is formed by three flat surfaces, and the apex of an arc with a D-shaped section is formed on the rear side from the two ends of the flat surfaces.

The inclined surface 2532 is formed so as to be inclined relative to the axis of the body portion and so as to extend from the hook connecting portion 2531 toward the back side (the opposite side of the abdominal portion 2533). The inclined surface 2532 forms an acute angle with respect to the surface of the abdominal portion 2533. This angle is preferably 30° to 60°. In addition, the inclined surface 2532 occupies about ⅓ the total length of the body portion 2503. However, the present invention is not limited to this. Furthermore, the inclined surface 2532 may be a flat or curved surface. Forming the inclined surface 2532 can prevent a tool from coming into contact with the drainage device 2500 during surgery, thereby providing a more user-friendly drainage device.

Figure 25B:
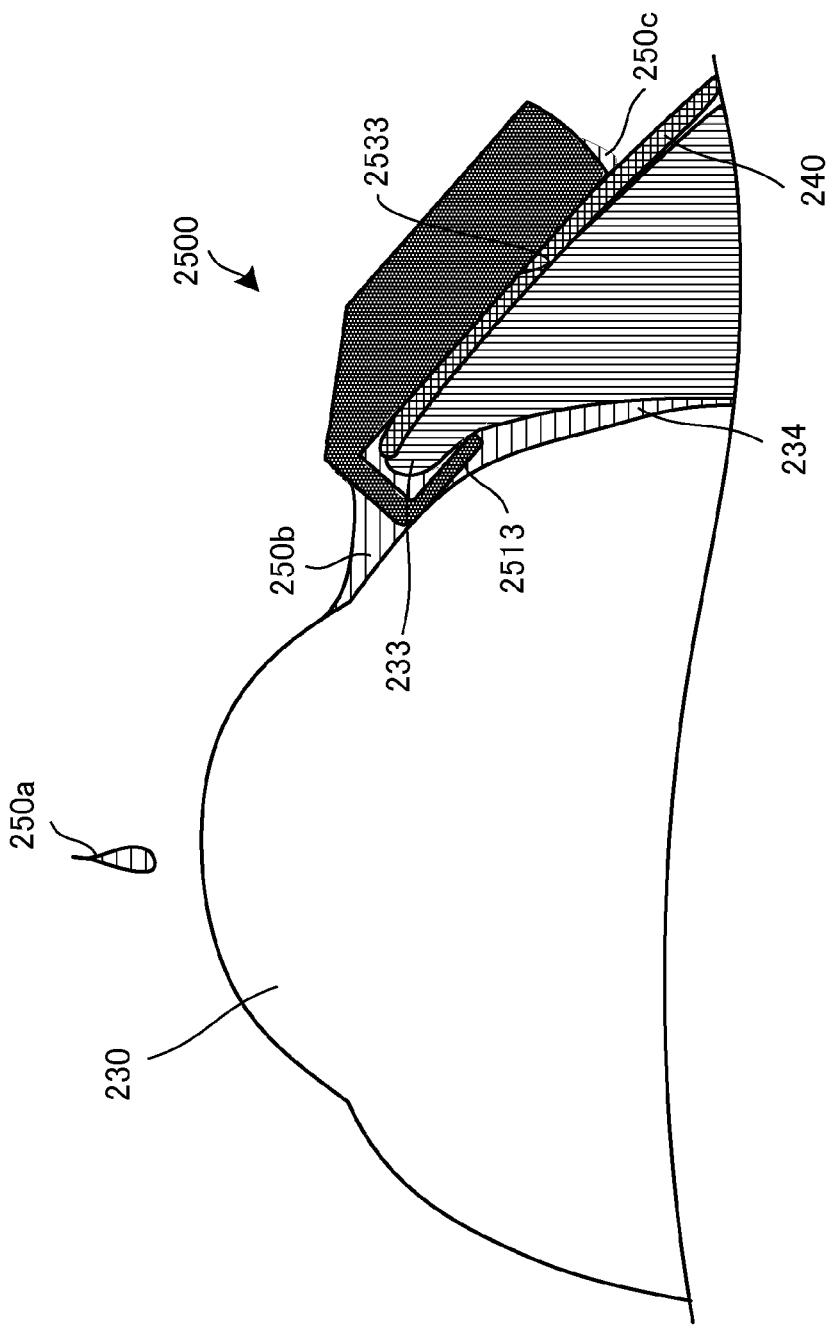
FIG. 25B is a sectional view showing a state of use of the drainage device according to the 12th embodiment of the present invention.

FIG. 25B is a sectional view of the palpebral fissure on which the drainage device 2500 is hooked and a peripheral portion of the palpebral fissure, taken along a plane passing through the medial ocular angle and the lateral ocular angle. Referring to FIG. 25B, the distal end portion of the hook portion 2501 is hooked on the conjunctival sac 234. The drainage device 2500 has a space formed larger (deeper) between the distal end portion 2513 of the hook portion 2501 and the abdominal portion 2533 of the body portion 2503 to further facilitate hooking on a lid margin 233 or a medical drape 240.

FIG. 25C is a sectional view of the drainage device 2500 according to this embodiment when viewed from the front. As shown in FIG. 25C, when viewed from the lid margin side, the body portion 2503 includes the abdominal portion 2533 having a bottom surface which comes into contact with the lid margin or medical drape and has a predetermined width and the inclined surfaces 2535 extending upward from the bottom surface toward the two side surfaces at obtuse angles. The internal angle defined by the bottom surface and each inclined surface 2535 is 100° to 170°, and preferably 135°. The gaps formed between the abdominal portion 2533, the inclined surfaces 2535, and the lid margin 233 function as capillary tubes to make a liquid 250 descend along the gaps due to capillary action.

With the above arrangement, the drainage device according to this embodiment can easily and stably discharge a liquid without using any aspirator.

13th Embodiment

Figure 26:
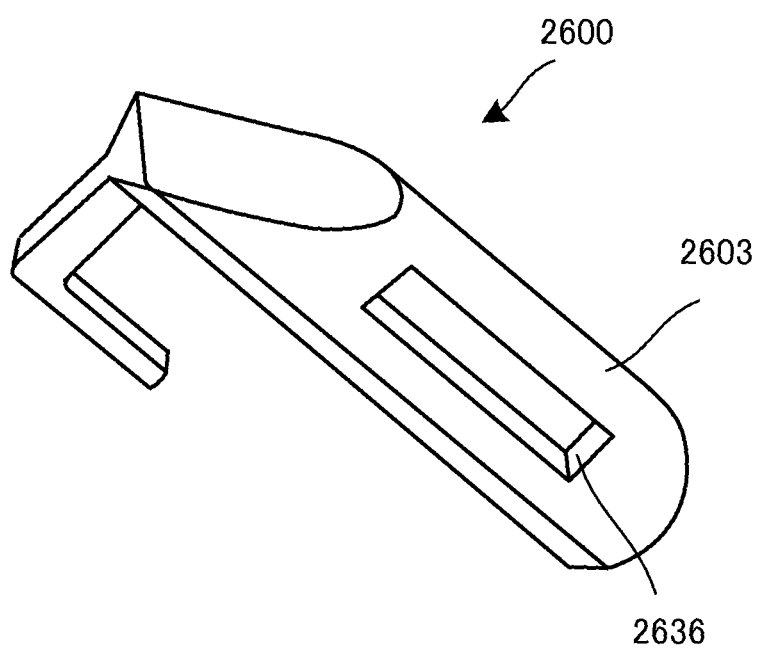
FIG. 26 is a perspective view showing the arrangement of a drainage device according to the 13th embodiment of the present invention.

A drainage device 2600 as the 13th embodiment of the present invention will be described with reference to FIG. 26. FIG. 26 is a perspective view showing the outer arrangement of the drainage device 2600 according to this embodiment. The drainage device 2600 includes a hole 2636 extending through a body portion 2603. The hole 2636 is formed in a direction perpendicular to the axis so as to be parallel to the abdominal side surface of the body portion 2603. Referring to FIG. 26, the hole 2636 has a rectangular parallelepiped shape. However, the inner surface of this hole may be a curved surface. In addition, the hole 2636 extends through the body portion 2603. However, a recess may be formed in the surface of the body portion 2603 instead of the through hole. Alternatively, a hole may extend through the tail side. The hole may have any shape as long as it allows to lock part of a lid retractor. This facilitates using the drainage device 2600 together with the lid retractor while locking it. Note that the tool which can be engaged with the hole 2636 is not limited to the lid retractor, and may include other types of surgical tools.

14th Embodiment

Figure 27:
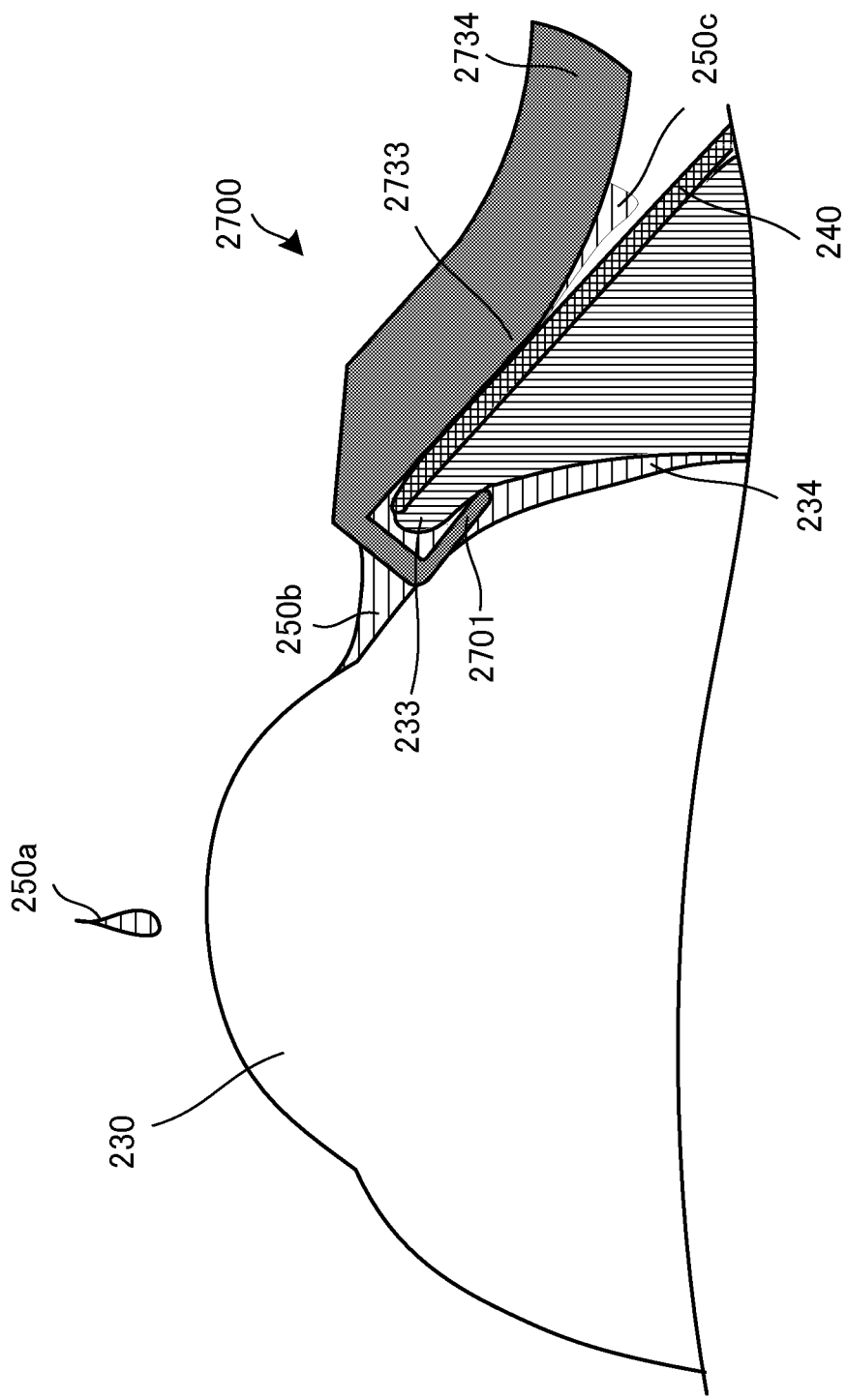
FIG. 27 is a perspective view showing the arrangement of a drainage device according to the 14th embodiment of the present invention.

A drainage device 2700 as the 14th embodiment of the present invention will be described with reference to FIG. 27. FIG. 27 is a sectional view showing a state of use of the drainage device 2700 according to this embodiment. The drainage device 2700 differs in arrangement from the 12th embodiment in that a tail portion 2734 of a body portion 2703 warps in a direction away from an abdominal portion 2733. When the tail portion 2734 warps in this manner, a liquid is discharged from a portion near the base of the tail portion 2734. Making the tail portion 2734 warp facilitates gripping the drainage device 2700 as a whole and allows the drainage device to be easily mounted on or removed from a patient.

Other Embodiments

According to each of the first to 14th embodiments described above, the hook portion and the body portion are integrally formed. However, the present invention is not limited to this. A hook portion and a body portion may be formed as discrete portions or may be formed from different materials. Although the present invention has been described with reference to the first to 14th embodiments, the present invention is not limited to the embodiments described above. Various changes that can be understood by those skilled in the art within the scope of the present invention can be made to the arrangements and details of the invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-41007 filed on Feb. 26, 2011, which is hereby incorporated by reference herein in its entirety.

The invention claimed is:

1. A drainage device for discharging a liquid retained in a palpebral fissure to the outside of the palpebral fissure, comprising:
    a hook portion configured to be hooked on a lid margin or a medical drape so as to independently retain said drainage device on the lid margin or the medical drape and to contact liquid in the palpebral fissure or overflowing from the palpebral fissure to form a start point of a flow path for the liquid, said hook portion having a proximal end and a distal end, the distal end of said hook portion comprising a first end of said drainage device and being formed in a spatula shape; and
    a body portion that extends from said hook portion and discharges the liquid guided by said hook portion,
    wherein said proximal end of said hook portion is adjacent to said body portion and extends from a first lateral side of said body portion to an opposing lateral side of said body portion, and
    wherein said body portion includes an abdominal portion and a tail portion, the tail portion comprising a second end of said drainage device and being configured to be disposed adjacent to and unattached to the lid margin or the medical drape, such that said body portion discharges the liquid after arrival thereof at a surface of said tail portion by making the liquid run along a gap between a lid margin side surface of said abdominal portion and the lid margin or the medical drape.

2. The drainage device according to claim 1, wherein a width of said hook portion having the spatula shape is smaller than a width of a thickest portion of said body portion.

3. The drainage device according to claim 1, comprising a connecting portion connecting the hook portion and the body portion, wherein said body portion includes an inclined surface inclined relative to an axis extending along the connecting portion.

4. The drainage device according to claim 3, wherein said body portion has a circular cross-section taken along a plane perpendicular to the axis.

5. The drainage device according to claim 3, wherein said body portion has a polygonal cross-section taken along a plane perpendicular to the axis.

6. The drainage device according to claim 1, wherein said body portion includes a grip portion on a rear side thereon.

7. The drainage device according to claim 1, wherein said proximal end of said hook portion is larger than said distal end of said hook portion.

8. The drainage device according to claim 1, wherein said body portion is tapered from the hook portion to the tail portion.

9. The drainage device according to claim 1, wherein said body portion includes a neck portion located between said hook portion and said body portion, the neck portion forming a horizontal plane in the area between said hook portion and said body portion.

10. The drainage device according to claim 1, wherein said hook portion comprises a bent portion that is formed to have a radius corner between said hook portion and said abdominal portion of said body portion.

* * * * *